United States Patent [19]
Kogure

[11] Patent Number: 5,672,305
[45] Date of Patent: Sep. 30, 1997

[54] METHOD OF MANUFACTURING MEDICAL PROSTHETIC ARTICLES

[76] Inventor: Yamato Kogure, 3-23-2, Masago, Niigata-shi, Japan

[21] Appl. No.: 635,296

[22] Filed: Apr. 19, 1996

Related U.S. Application Data

[63] Continuation-in-part of Ser. No. 265,201, Jun. 24, 1994, abandoned.

[30] Foreign Application Priority Data

| Jun. 25, 1993 | [JP] | Japan | 5-155604 |
| Mar. 11, 1994 | [JP] | Japan | 6-79139 |
| Mar. 17, 1994 | [JP] | Japan | 6-87171 |

[51] Int. Cl.$^6$ .......... B29C 33/10; B29C 33/56; B29C 45/34
[52] U.S. Cl. .......... 264/102; 249/54; 264/328.1; 264/338
[58] Field of Search .......... 264/17, 39, 102, 264/328.1, DIG. 30; 249/54; 425/546, DIG. 11; 264/337, 338

[56] References Cited

U.S. PATENT DOCUMENTS

| 1,244,257 | 10/1917 | Sweetnam | 249/54 |
| 2,243,835 | 6/1941 | Brunner et al. | 425/546 |
| 2,274,186 | 2/1942 | Brace | 249/54 |
| 2,790,998 | 5/1957 | Dimmer | 425/DIG. 11 |
| 3,527,861 | 9/1970 | Weinstein et al. | 249/54 |
| 3,623,541 | 11/1971 | Schmitz | 249/54 |
| 4,359,435 | 11/1982 | Kogure | 264/328.16 |
| 5,302,104 | 4/1994 | Ueda | 425/DIG. 11 |
| 5,324,186 | 6/1994 | Bakanowski | 264/17 |
| 5,405,405 | 4/1995 | Love | 425/DIG. 11 |

FOREIGN PATENT DOCUMENTS 57-2023  1/1982  Japan.

Primary Examiner—Jill L. Heitbrink
Attorney, Agent, or Firm—Quarles & Brady

[57] ABSTRACT

A method of manufacturing a medical prosthetic article by injecting a thermoplastic resin into the cavity of a plaster mold, comprising the steps of: confining first and second plaster molds having porous structures respectively in first and second mold bodies made dividable from each other, the first and second plaster molds defining therein a cavity having first and second inner faces, a contour of a medical prosthetic article to be molded, a sprue runner communicating with the cavity, and an air vent communicating with the cavity; sealing up the cavity not only from the ambient air but also from the porous structures of the first and second plaster molds, when the first and second mold bodies are closed; evacuating the cavity through the air vent; and injecting a thermoplastic resin through the sprue runner into the cavity under a predetermined degree of vacuum.

7 Claims, 21 Drawing Sheets

METHOD OF MANUFACTURING MEDICAL PROSTHETIC ARTICLES

CROSS-REFERENCES TO OTHER APPLICATIONS

This is a continuation-in-part application of U.S. patent application Ser. No. 08/265,201 filed Jun. 24, 1994, now abandoned.

BACKGROUND OF THE INVENTION

1. Field of the Invention

The present invention relates to a method of molding a medical prosthetic article and, more particularly, to a molding method of manufacturing a medical prosthetic article by charging a cavity of a sealed plaster mold under a predetermined vacuum with a resin.

2. Description of the Related Art

It has been known in the prior art that medical prosthetic articles such as bedded artificial teeth or artificial bones or limbs to be fitted in human bodies are molded of resins. For this molding process with resins, there has been practiced an injection molding method which uses a plaster mold fitted in a working mold of a metal or the like. As disclosed by us in Japanese Patent Publication No. 2023/1982, on the other hand, the aforementioned injection molding method is carried out by injecting a resin into the cavity of a plaster mold formed in the working mold.

However, this method has been accompanied by a problem that the molten resin may be encountered by a non-homogenous flow or by incorporation of gases produced during the molding process, because the medical prosthetic article often has a complicated shape and/or portions of different thicknesses. Another problem is that the resultant molding may be encountered by a strain such as a warp or twist due to the shrinkage of the resin cooled. Specifically, in case the medical prosthetic article is exemplified by bedded artificial teeth, its portion corresponding to the palatal surface of an upper jaw has to be made as thin as about 0.5 to 1.2 mm whereas its tooth socket head is made as thick as about 10 mm. Thus, the bedded artificial teeth are highly different in their local thicknesses to that the denture base is subjected to a molding strain to float or warp from the inner face of the mold. This molding strain has to be manually corrected by the operator.

The main stream of a material for manufacturing a dental prosthetic article such as artificial teeth is acrylic resins. Specifically, powder of methyl acrylate polymer and a liquid of methyl acrylate monomer are admixed and preliminarily polymerized. This mixture is poured into a plaster mold for several minutes, and this plaster mold is heated for as long as forty minutes to one hour and thirty minutes to properly polymerize and mold the mixture.

Due to an incomplete polymerization, however, this molding method allows the residual monomer to be dissolved into the mouth so that it is deficient in the bio-safety. Another problem is that the manufacture efficiency is deteriorated because of the long time required for the molding.

We have tried for many years to solve those problems and have proposed a method of molding an artificial tooth by injecting a thermoplastic resin into a plaster mold, as disclosed in U.S. Pat. No. 4,359,435 which is based upon the technical concept of separating the polymerization and the molding such that a 100% polymerized thermoplastic resin is subjected to only the molding treatment. According to this method, no monomer is left non-polymerized to provide a high bio-safety, and the resin is molded for as short as about one minute so that the manufacture efficiency is remarkably satisfactory.

Here, the thermoplastic resin is cooled and solidified instantly after it has been injected into the plaster mold. Thus, the charging of the mold with the thermoplastic resin has to be ended for an extremely short time under a high injection pressure. The bedded artificial tooth has to be molded conforming to the dentiform of each patient so that it has a local thickness difference as large as 0.5 to 10.0 mm. As a result, if the injection is made under the aforementioned high pressure, the resin flow becomes uneven to cause a molding distortion or strain. Thus, this strain may be released as the time elapses, to invite a later deterioration in the fitting properties in the mouth.

Moreover, gases, as generated from the molten resin, are entrained by the resin to produce fine bubbles thereby to lower the density.

Therefore, we have investigated in various ways to solve those problems and can succeed in providing a method of manufacturing dense and excellently fitting dental prosthetic articles of high qualities by employing a thermoplastic resin.

According to the gist of the present invention, the cavity in the first and second plaster molds, which have seal layers on their inner faces and which are sealed up from the ambient ar and the porous plaster structures, is evacuated through an air vent, and a thermoplastic resin through a sprue runner into the cavity.

The evacuation and the smooth inner faces of the molds can smooth the flow of the molten resin and can prevent the entrainment of the gases.

As a result, the injection pressure of the prior art as high as 230 Kg/cm$^2$ can be lowered to 20 Kg/cm$^2$ so that the residual stress of the moldings can be accordingly reduced to reduce the molding strain remarkably without lowering the density, as plotted in the later-described graphs. Thus, it is possible to provide a highly fitting and strong dental prosthetic article while retaining the effects of high bio-safety and manufacture efficiency. Thanks to the lowered injection pressure, it is possible to provide a small-sized sample apparatus for practicing the manufacture method.

As the technique for manufacturing the artificial tooth by the vacuum-molding method, there is known U.S. Pat. No. 5,324,186 to Bakanowski. According to this technique, as described above, the acrylic material is subjected to the polymerization and the molding treatment at the same time. The plaster molds are charged, while being evacuated, with the acrylic material by the pneumatic type simple injector for several minutes so that the acrylic material may flow to every corners of the cavity. After this, the molds are heated for a long time to polymerize and solidify the acrylic material.

However, Bakanowski has completely failed to take consideration into the subject matter of the present invention, i.e., the molding strain which would be caused by injecting the thermoplastic resin under a high pressure. Specifically, Bakanowski has resorted to the pneumatic type simple injector for the acrylic material injection operation of several minutes so that it is short of the pressure retention to leave some portions uncharged. This shortage of the pressure retention is supplemented by the evacuation so that the molding operation cannot be effected without the supplementation. Hence, the evacuation, as employed Bakanowski, is no more than an auxiliary force for assisting the flow of the acrylic material. Thus, the evacuation is not employed unlike the present invention for manufacturing artificial teeth of higher qualities.

As another technique for applying and solidifying a resin on the plaster mold surfaces, there is known U.S. Pat. No. 5,302,104 to Ueda. According to this technique, a thermoplastic resin is injected under a high injection pressure into the plaster molds while aiming at solving the problem of the molding strain. However, the method for solving this problem is effected merely by heating the flask before the indexing operation. This method requires such a long heating step that its working efficiency is low, and achieves little effect upon the molding strain. Specifically, Ueda has neither disclosed nor hinted the vacuum molding method using the plaster molds. What is disclosed is to prevent the thermoplastic resin from being deteriorated by the moisture content in the plaster molds by applying and solidifying a photosetting region to the surfaces of the plaster molds at a step before the resin injection so as to shorten the plaster drying time. Ueda has not intended unlike the present invention to seal the mold cavity from the porous plaster structures for the vacuum molding operation.

In other words, the disclosure of Ueda is satisfactory when the injection is performed for the insufficiently dry plaster molds. This is because the injection is not performed according to the ordinary method before the plaster molds are sufficiently dried up, so that the moisture content in the plaster molds raises no problem at the ordinary injection molding time but not in the vacuum injection molding.

Thus, any combination of the existing two prior arts could not attain the effect that the injection pressure as high as 230 Kg/cm$^2$ can be lowered to 20 Kg/cm$^2$ to reduce the residual stress in the moldings and accordingly the molding strain, as illustrated in the graphs, without lowering the density.

SUMMARY OF THE INVENTION

It is, therefore, an object of the present invention to provide a method of manufacturing a medical prosthetic article while suppressing a molding strain.

In order to achieve these objects, according to an aspect of the present invention, there is provided a method of manufacturing a medical prosthetic article by injecting a thermoplastic resin into the cavity of a plaster mold, comprising the steps of: confining first and second plaster molds having porous structures respectively in first and second mold bodies made dividable from each other, the first and second plaster molds defining therein a cavity having first and second inner faces, a contour of a medical prosthetic article to be molded, a sprue runner communicating with the cavity; sealing up the cavity not only from the ambient air but also from the porous structures of the first and second plaster molds, when the first and second mold bodies are closed; evacuating the cavity through the air vent; and injecting a thermoplastic resin through the sprue runner into the cavity under a predetermined degree of vacuum.

BRIEF DESCRIPTION OF THE ACCOMPANYING DRAWINGS

Other objects, features and advantages of the present invention will become apparent from the following description to be made with reference to the accompanying drawings, in which.

DESCRIPTION OF THE PREFERRED EMBODIMENTS

Figure 2:
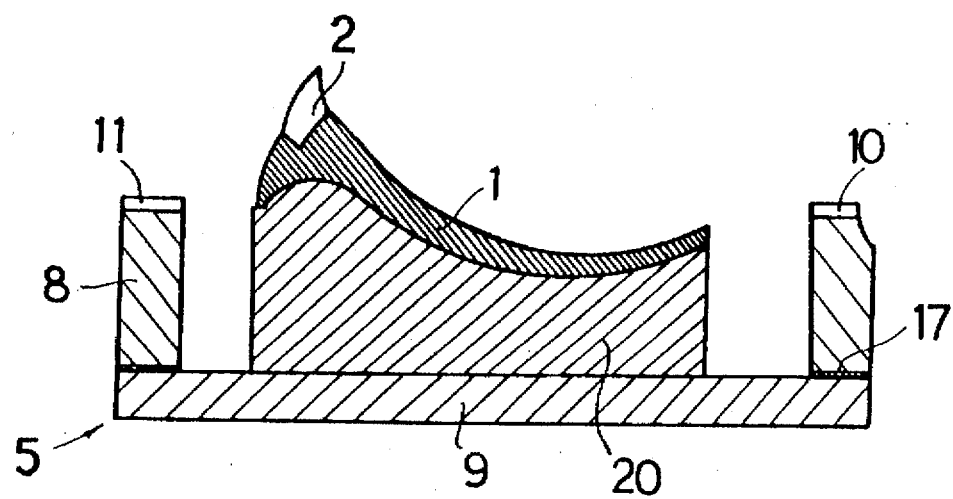
FIG. 2 is a vertical section showing the first embodiment of the present invention.
Figure 3:
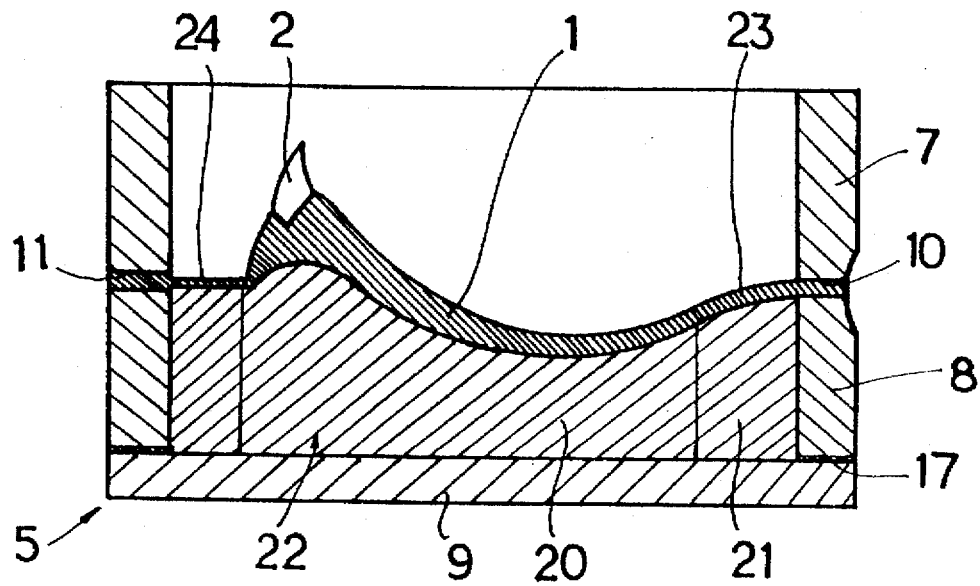
FIG. 3 is a vertical section showing the first embodiment of the present invention.
Figure 4:
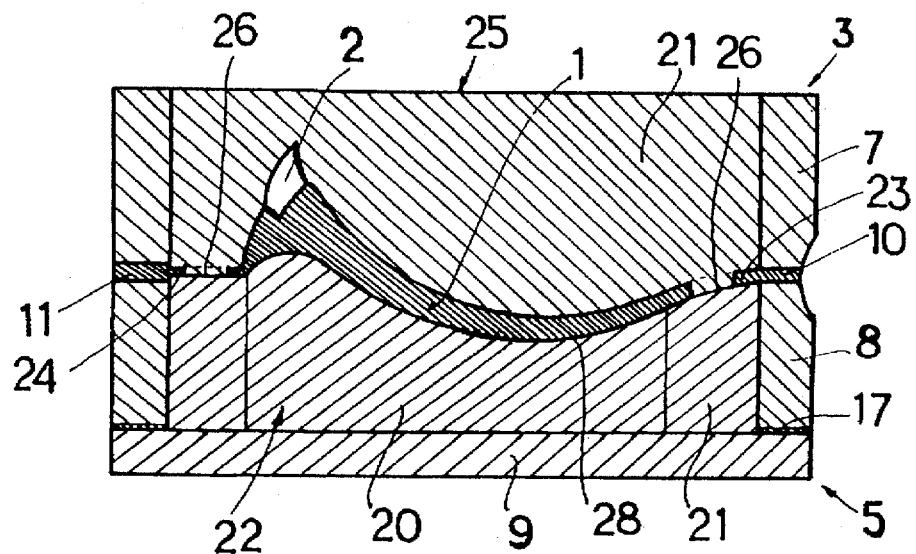
FIG. 4 is a vertical section showing the first embodiment of the present invention.
Figure 5:
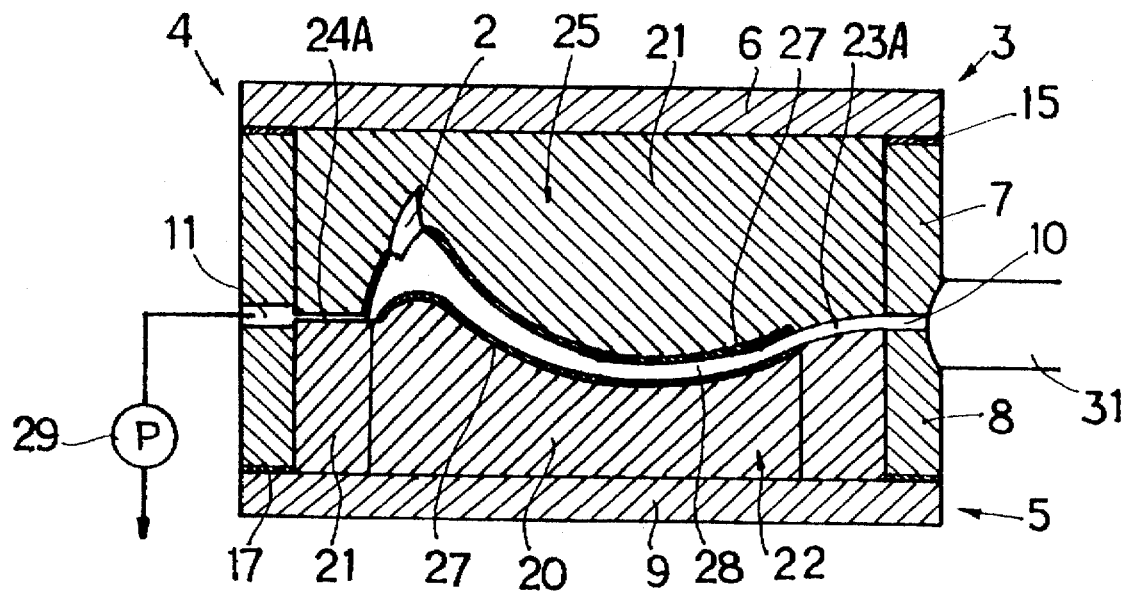
FIG. 5 is a vertical section showing the first embodiment of the present invention.

The present invention will be described in the following in connection with its embodiments with reference to the accompanying drawings. In a first embodiment of the present invention, as shown in FIGS. 1 to 11, a model having the same shape as that of a medical prosthetic article such as bedded artificial teeth is formed of a thermoplastic material such as wax, synthetic wax or a soft resin. This model 1 is arranged in advance with artificial teeth 2. There is prepared a pressure-resisting working mold 3 which is made of a metallic material. This working mold 3 is constructed of a first mold body 4 and a second mold body 5. Of these, the first mold body 4 is composed of a top cover member 6 or a first separate mold member and an upper ring member 7 or a second separate mold member, and the second mold body 5 is composed of a lower ring member 8 or a third separate mold member and a bottom cover member 9 or a fourth separate mold member. The working mold 3 is formed with an injection port 10 and a discharge port 11 at its abutting faces between the upper and lower ring members 7 and 8. On the other hand, the working mold 3 is equipped with fixing members 14 including bolts and nuts for uniting the first and second mold bodies 4 and 5 when positioned by positioning pins 12 and positioning holes 13. Moreover, the working mold 3 is equipped with a sealing structure which is composed of a ring-shaped sealing members made of a thin metallic seat or synthetic resin seat. This sealing structure is composed of: a first sealing member 15 between the abutting faces of the top cover member 6 and the upper ring member 7; a second sealing member 16 between the abutting faces of the upper ring member 7 and the lower ring member 8; and a third sealing member 17 between the abutting faces of the lower ring member 8 and the bottom cover member 9. Of these: the first sealing member 15 is adhered to the top cover member 6; the second sealing member 18 is adhered to the upper ring member 7; and the third sealing member 17 is adhered to the bottom cover member 9. Moreover, these sealing members 15, 16 and 17 are individually formed with positioning/fixing holes 18, and the second sealing member 16 is divided by injection/discharge cutouts 19. With the first and second mold bodies 4 and 5 being disassembled, still moreover, the model 1 is fixed through a plaster bed 20 in the second mold body 5, as shown in FIG. 2, and the model 1 is primarily buried in the second mold body 5 by injecting a plaster wax 21, as shown in FIG. 3, to form a second plaster mold 22 as the plaster wax 21 solidifies. As shown in FIG. 3, the model 1 is connected on one hand to the aforementioned injection port 10 via a sprue runner 23 which is made of the aforementioned thermoplastic material, and on the other to the aforementioned discharge port 11 via an air vent 24 which is also made of the thermoplastic material. As shown in FIG. 4, the upper ring member 7 is then positioned on and assembled with the lower ring member 8, and these two upper and lower ring members 7 and 8 are united by the fixing members 14. The plaster wax 21 is injected into the upper ring member 21 to bury the model 1 secondarily, to form a first plaster mold 25 as the plaster wax 21 solidifies. After the plaster wax 21 has solidified, the upper ring member 7 is disassembled, and the first and second plaster molds 25 22 are divided through a parting face 26 of the plaster 21. The model 1, the sprue runner 23 and the air vent 24 are melted and discharged and are washed away with hot water or the like. The plaster molds 25 and 22 are dried and then formed with sealing layers 27 on their inner faces. These sealing layers 27 are prepared by applying and drying a surfacing agent which has such a hardness and gas-tightness as can stand the injection pressure of the resin. As shown in FIG. 5, the first and second mold bodies 4 and 5 are assembled and united through the fixing members 14 to bring the first and second plaster molds 25 and 22 into a closed state. In this state, there are formed a cavity 28 contoured to the shape of the denture bed, a sprue runner 23A for providing a resin passage, and an air vent 24A for providing a discharge passage of the air/gases. Moreover, the individual abutting portions of the top cover member 6, the upper and lower ring members 7 and 8 and the bottom cover member 9 are made gas-tight by the first, second and third sealing members 15, 16 and 17, and the cavity 28 is also made gas-tight by the sealing layers 27. A vacuum pump 29 is connected to the aforementioned discharge port 11.

Figure 1:
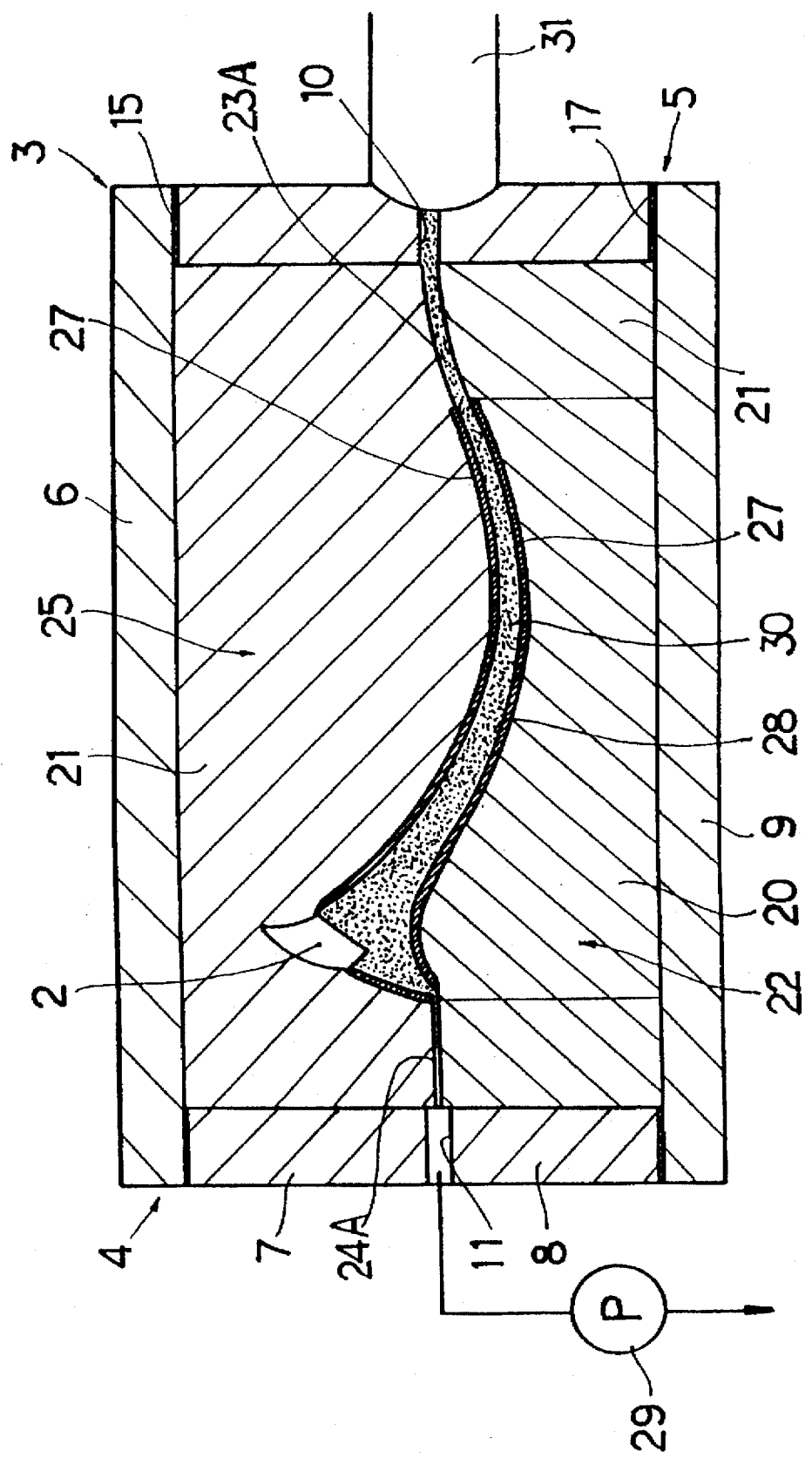
FIG. 1 is a vertical section showing a first embodiment of the present invention.

Reverting to FIG. 1, a molten high-molecular resin 30 is injected from the aforementioned injection port 10 into the cavity 28 by an injection member 31 of an injection molding machine. At this time, the charge of the resin 30 is performed after having evacuated or while evacuating the cavity 28 by the action of the vacuum pump 29. Specifically, this vacuum pump 29 is run before the injection of the resin 30 so that the resin 30 may be injected into the cavity 28 which has been or is being evacuated to a vacuum lower than the atmospheric pressure. The vacuum pump 29 may have its capacity suitably selected by considering the volume of the cavity 28. Here, the degree of vacuum of the cavity 28 is set to 500 to 0.00001 Torrs, preferably to 20 to 0.00001 Torrs. This range is determined because the moldability is hard to improve for a vacuum level lower than 500 Torrs whereas the evacuating system and the sealing device grow expensive and poor in practice for a degree of vacuum higher than 0.00001 Torrs. Since, moreover, the air in the gas-tight cavity 28 and the gases to be released from the molten resin 30 are discharged from the aforementioned discharge port 11 by the evacuation, the resin having filled up the cavity 28 can be restrained from containing the gases. Moreover, the resin 30 has its flow smoothed by the vacuum prevailing in the cavity 28 so that is can ooze into every corners of the cavity 28. As a result, the molding has its residual stress reduced after cooled. Then, the working mold 3 is disassembled, and the plaster molds 25 and 22 are crushed to take out the molding. When this molding is cleared of the resin 30 at the sprue runner 23A and the air vent 24A, it is possible to produce the molding of bedded artificial teeth having its molding strain suppressed.

Thus, according to the present embodiment, the resin 30 can be charged into the cavity 28 as evacuated or being evacuated in the plaster molds 25 and 22. Since the air and the gases are sucked and discharged from the cavity 28 via the discharge port 11, the resin 30 having filled up the cavity 28 is restrained from containing the gases and so on, and the resin 30 is allowed to smoothly flow into every corners of the cavity 28 so that the residual stress can be reduced in the cooled molding. Thanks to the molding process after having evacuated or while evacuating the cavity 28, moreover, the resin injection pressure, i.e., the injection pressure of the injection molding machine can be lowered so much. For example, the injection pressure of 230 Kg/cm² without the evacuation can be lowered to about 100 Kg/cm² in case the degree of vacuum in the cavity 28 is lowered to 0.0001 Torrs by the evacuation. As a result, the capacity required of the molding machine can be lowered to reduce the size of the molding machine. At the same time, the linear expansion and accordingly the residual stress are reduced to suppress the strain of the resultant molding. Thanks to the molding process after having evacuated or while evacuating the cavity 28, still moreover, the resin molding temperature can be lowered to reduce the thermal expansion so that thermal shrinkage can be reduced to improve the molding accuracy and to prevent deterioration of the color of the molding. Thus, it is possible to produce a highly accurate molding.

According to the present embodiment, since the sealing layers 27 are formed on the inner faces of the plaster molds 25 and 22 to seal the cavity 28, the air contained in the molds 25 and 22 can be restrained from stealing into the cavity 28 even with the suction of the vacuum pump 29. As a result, it is possible to omit one or two of the first to third sealing members 15 to 17, especially the first and third sealing members 15 and 17. Moreover, since the sealing layers 27 are formed by the coating of the surfacing agent, their smooth surfaces are transferred to the surfaces of the resin 30 so that a lustrous molding can be produced.

In the case of a plaster mold, generally speaking, due to the properties of the plaster material, the resin molding will have different thicknesses at their individual portions, or the resin molding will be difficult to correct even if its individual portions have a dispersion in the resin shrinkage as its structure grows complex. Thus, the resultant resin molding has an accordingly low accuracy. According to the present embodiment, however, the coating of the sealing layers 27 can be given thicknesses according to the degree of resin shrinkages at the individual portions of the molding so that the molding can have its size easily corrected.

For the thermoplastic resin such as the polycarbonate resin, the following formula holds if the loading stress is within the elastic limits:

*Residual Stress=E×Molding Strain*

Figure 33:
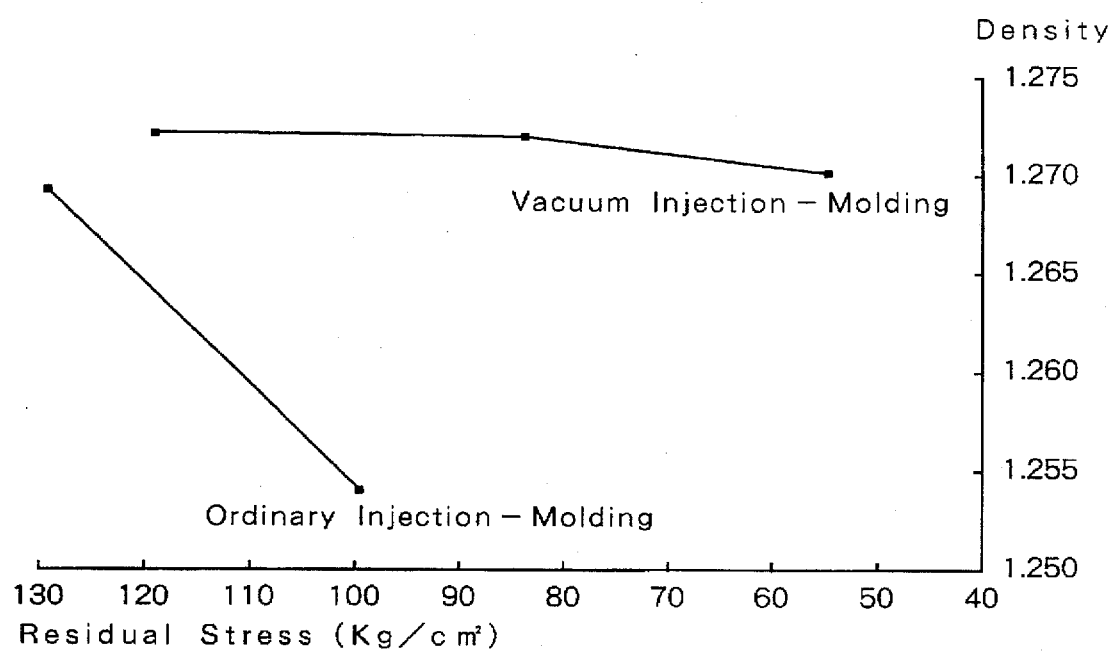
FIG. 33 is a graph plotting a density against a residual stress for comparing the vacuum injection-molding of the present invention with the ordinary injection-molding.

(wherein E is a proportional constant). Generally, the density or quality of an article produced by ordinary injection-molding degrades the molding strain is reduced. By comparison, the molding strain or residual stress or articles produced using the vacuum injection-molding method of the present invention can be reduced by about 60% without lowering the density. Empirical test results directed to this feature may be found in FIG. 33 which shows that density of articles manufactured using ordinary thermal injection molding drops off dramatically as residual stress decreases from 130 to 100 Kg/cm². By comparison, FIG. 33 shows that articles manufactured with the vacuum injection molding method of the present invention maintain a high density as residual stress is varied from between about 120 Kg/cm² to about 55 Kg/cm². Thus, the present invention allows residual stress to be reduced for the purpose of maintaining high molding accuracy for the prosthetic article, while simultaneously maintaining high density.

Significantly, it has also been found that use of the vacuum thermal resin injection method of the present invention allows resin injection pressure to be decreased from approximately 230 Kg/² to about 100 Kg/cm² without any significant sacrifice in the resulting resin density. Normally, thermoplastic resin is injected under high pressure, e.g., 230 Kg/cm² because resin density has been found to abruptly drop if injection pressure is substantially lowered. However, the present invention allows high resin density to be maintained with reduced region injection pressure. As a result, the capacity required of the molding machine can be lowered so as to reduce the size of the molding machine.

Further, warp or twist may arise in thermal resin injection dental prosthetic due to strain caused by shrinkage of the resin as it is cooled. The vacuum injection method of the present invention permits this undesirable problem to be overcome by use of lower resin molding temperatures. This reduces thermal expansion so that thermal shrinkage can be reduced to improve molding accuracy and to prevent deterioration of the color of the molding.

Figure 34:
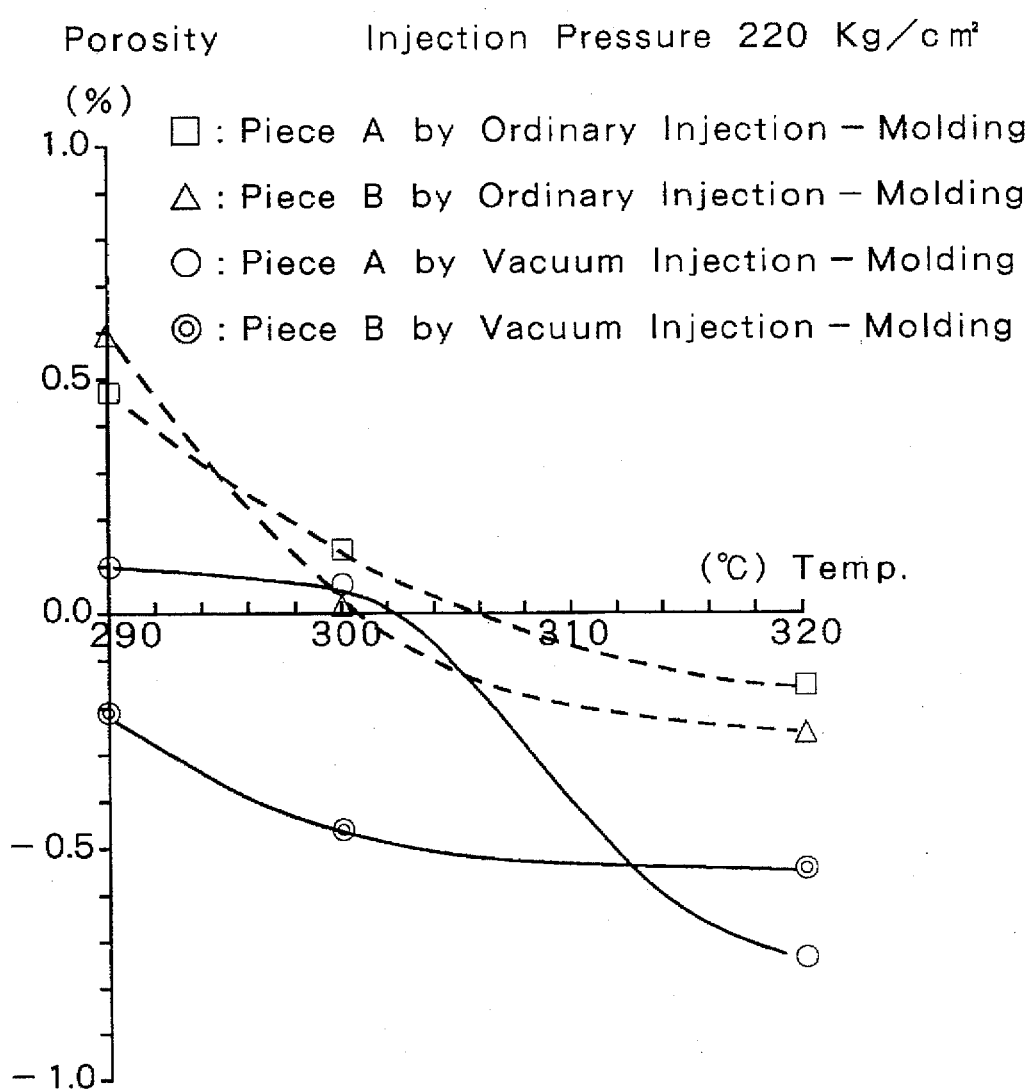
FIG. 34 is a graph plotting a porosity against a temperature for comparing the vacuum injection-molding of the present invention with the ordinary injection-molding.
Figure 35:
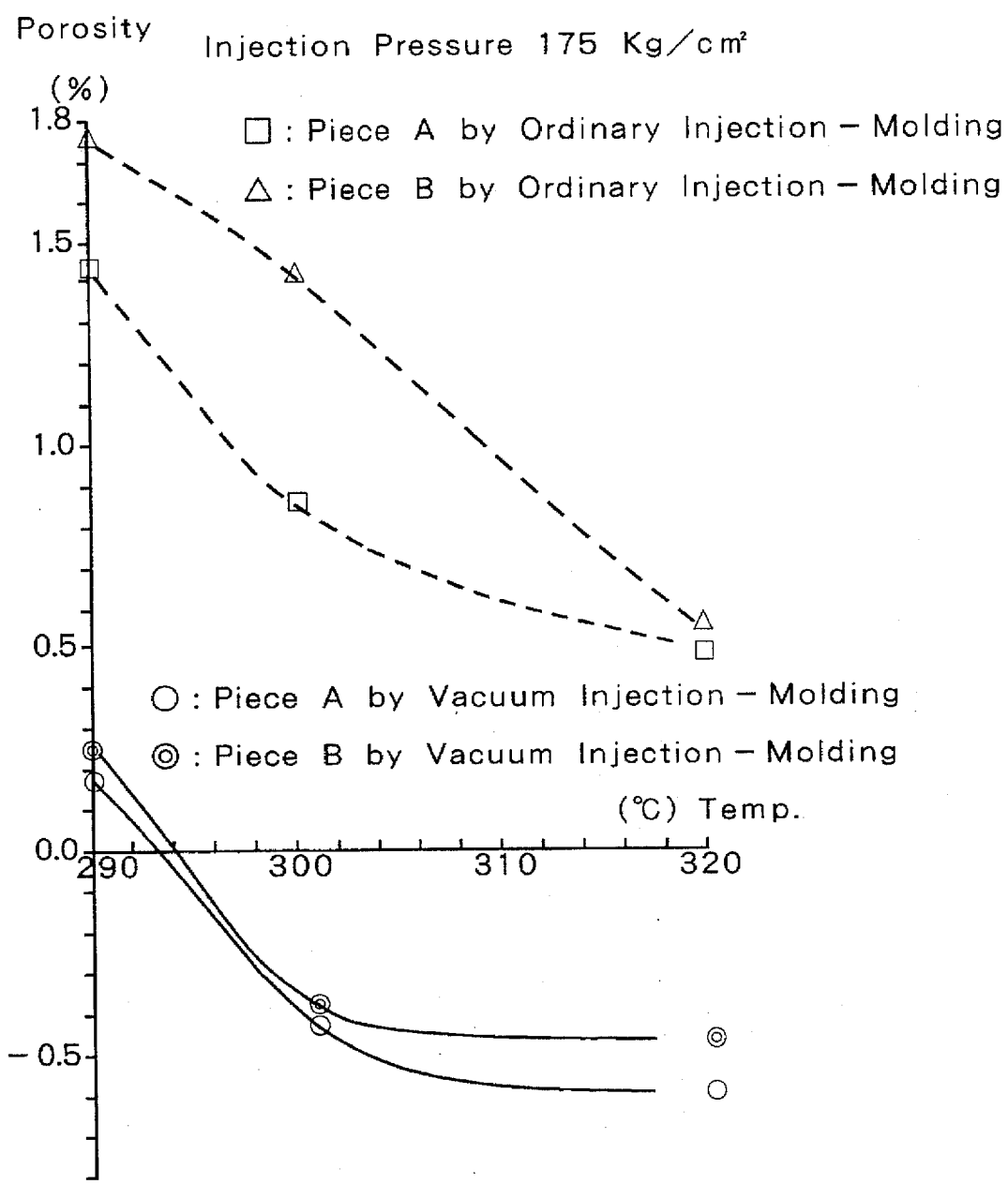
FIG. 35 is similar to FIG. 34 but under a different injection pressure.

FIGS. 34 and 35 illustrate the significant advantages obtained with respect to porosity by use of the vacuum system of the present invention as compared to ordinary injection molding. It is apparent from these Figures that the porosity of the vacuum injection molding method is reduced substantially as compared to that of the ordinary injection molding method. Thus, the significant advantages obtained with the method of the present invention are apparent.

Thus, in the present embodiment, the inner faces of the first and second plaster molds 25 and 22 are sealed up, and the cavity 28 in the plaster molds, as sealed from the ambient air and the porous plaster structures, is evacuated through the air vent 24A. The thermoplastic resin 30 is injected into the cavity 28 through the sprue runner 23A.

As a result, the molten resin is permitted to flow smoothly by the evacuation and the smooth surfaces of the sealed inner faces of the molds and is prevented from entraining the gases.

As a result, the injection pressure can be lowered from the high pressure of 230 Kg/cm² of the prior art to 20 Kg/cm² so that the residual stress in the moldings can be reduced to reduce the molding strain remarkably, as illustrated in FIG. 33, without lowering the density. Thus, it is possible to provide a high fitting and strong dental prosthetic article of high quality while maintaining the effects of high bio-safety and excellent manufacture efficiency. Thanks to the drop in the injection pressure, moreover, a small-sized and simple molding machine can be provided at a reasonable price.

Figure 12:
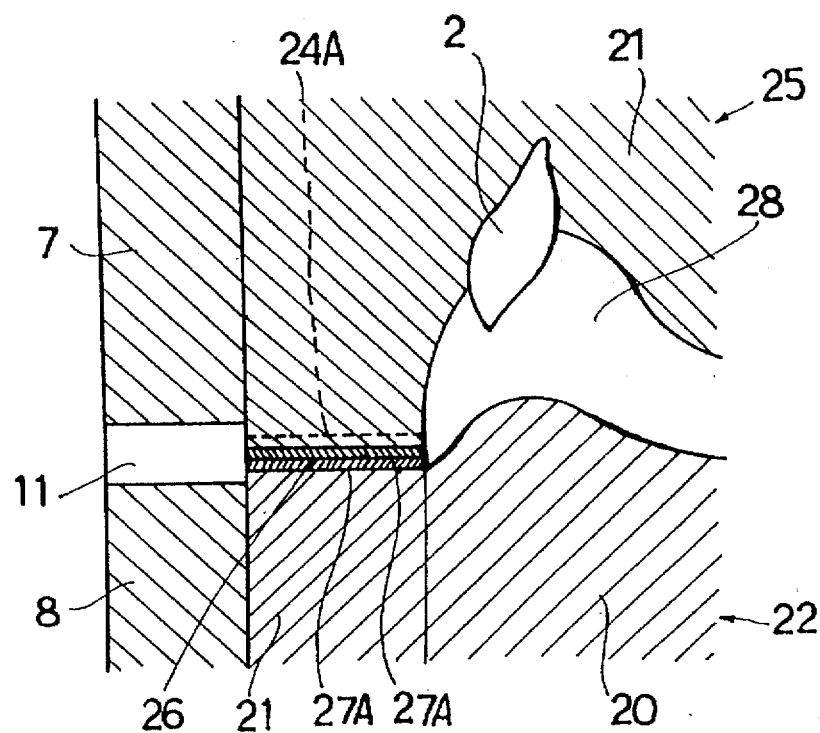
FIG. 12 is an enlarged vertical section showing an essential portion of a second embodiment of the present invention.
Figure 13:
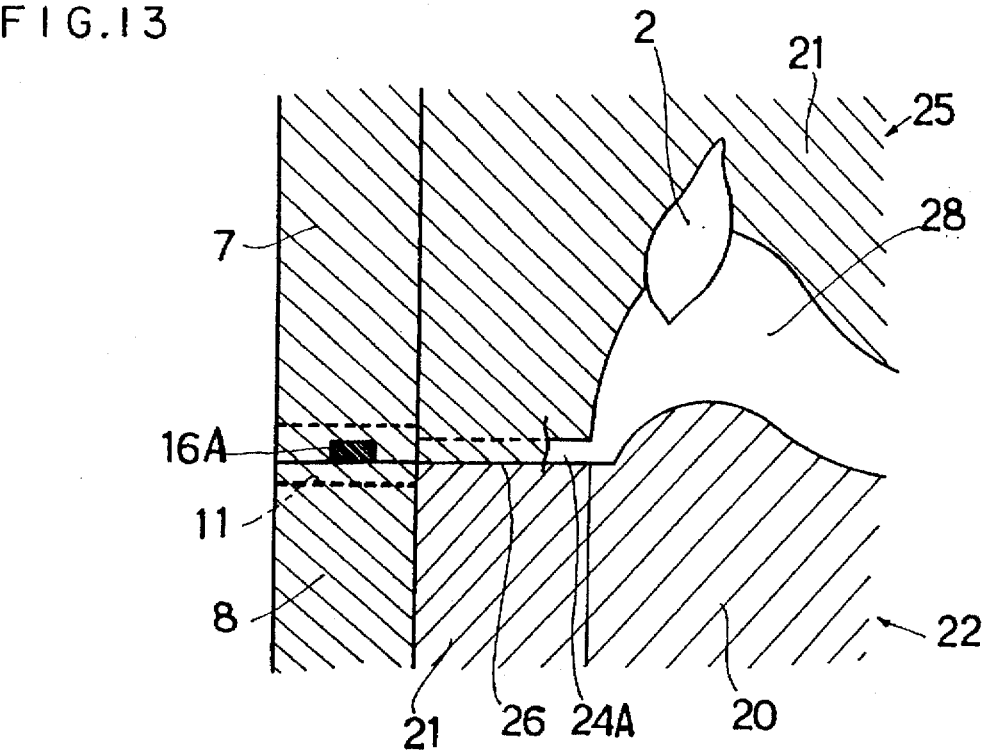
FIG. 13 is an enlarged vertical section showing an essential portion of a third embodiment of the present invention.

Turning to FIG. 12 showing a second embodiment of the present invention, the same portions as those of the foregoing first embodiment are designated at the common reference numerals so that their repeated description is omitted. Specifically, the first and second plaster molds 25 and 22 are individually formed with sealing layers 27A on their abutting faces. Thus, in the present embodiment, the cavity 28 in the plaster molds 25 and 22 can be charged under a predetermined vacuum with the resin 30. As a result, the air and gases in the cavity 28 can be sucked and discharged from the discharge port 11 so that the resin 30 having filled up the cavity 28 can be restrained from containing the aforementioned gases or the like. At the same time, the resin 30 can be allowed to smoothly flow into every corners of the cavity 28 to reduce the residual stress in the cooled molding. Moreover, as the resin injection pressure can be lowered as in the foregoing embodiments, the molding machine can be small-sized to suppress the residual stress. Since the molding temperature can be lowered, still moreover, it is possible to produce a molding which can have excellent molding accuracy and a clear color. According to the present embodiment, on the other hand, thanks to the sealing layers 27A formed on the abutting faces of the plaster molds 25 and 22, one or two of the first to third sealing members 15 to 17 can be omitted.

Figure 14:
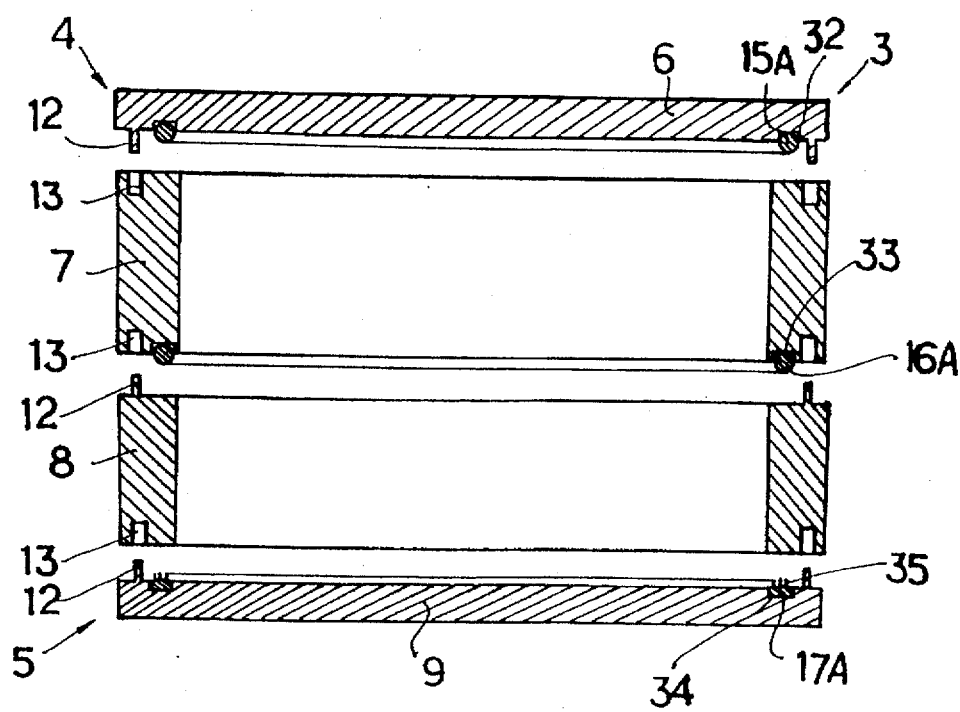
FIG. 14 is an exploded vertical section showing a working mold according to a third embodiment of the present invention.
Figure 15:
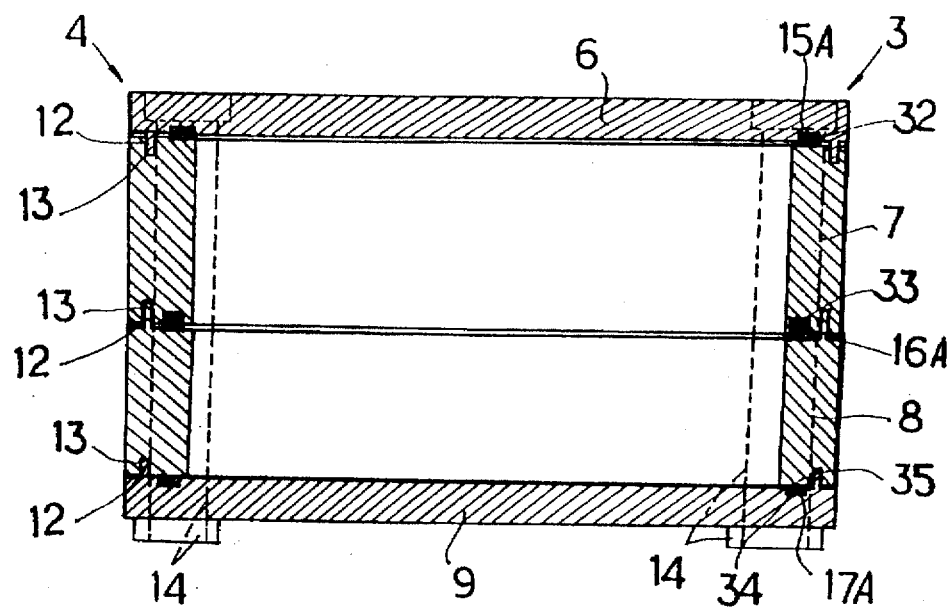
FIG. 15 is an exploded vertical section showing the working mold according to the third embodiment of the present invention.
Figure 16:
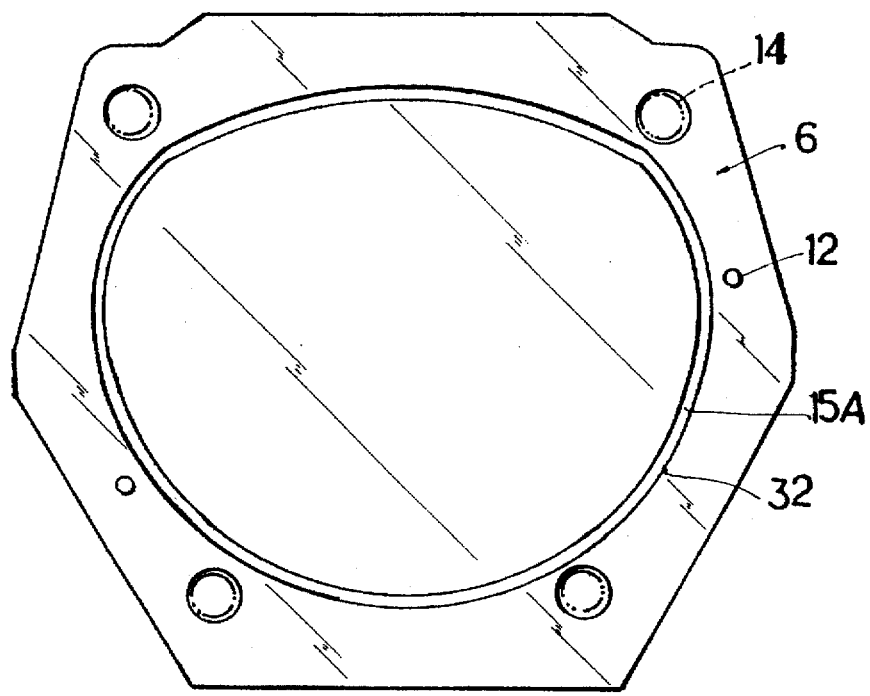
FIG. 16 is a top plan view showing a top cover member of the working mold according to the third embodiment of the present invention.
Figure 17:
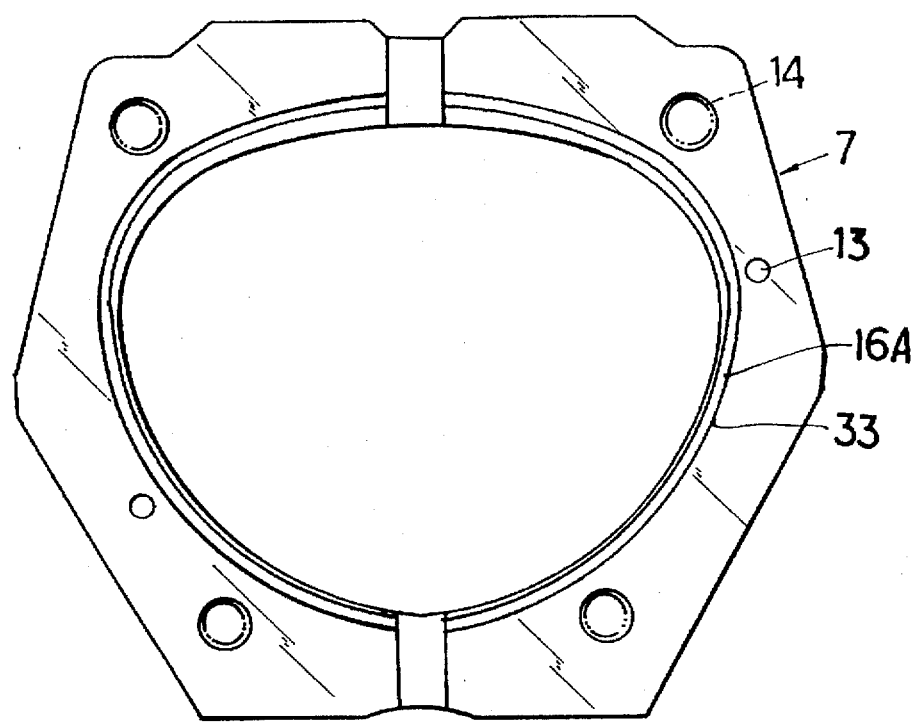
FIG. 17 is a top plan view showing an upper ring member of the working mold according to the third embodiment of the present invention.
Figure 18:
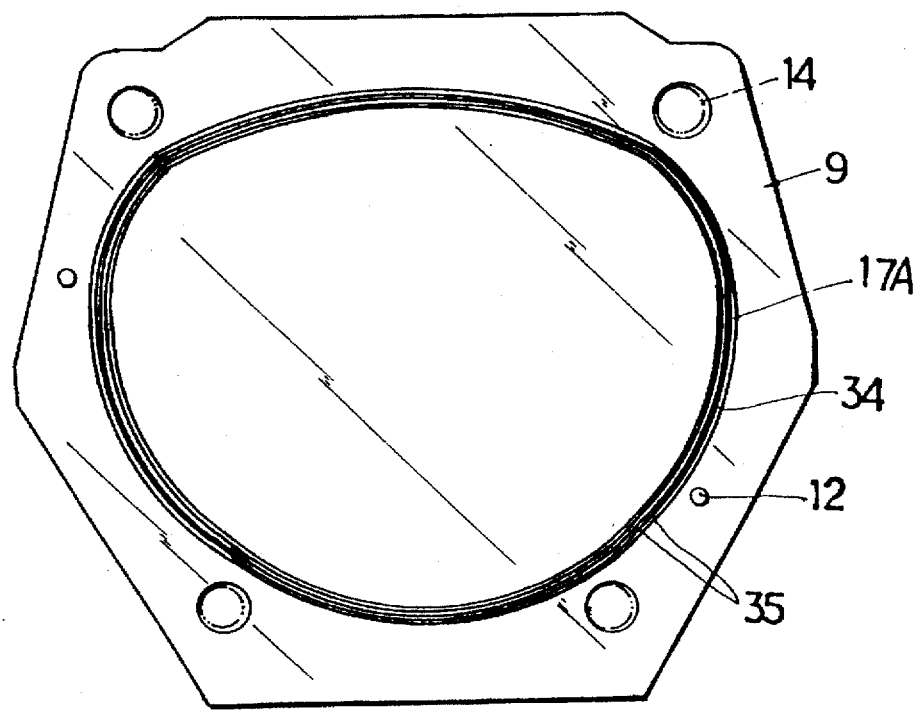
FIG. 18 is a top plan view showing a bottom cover member of the working mold according to the third embodiment of the present invention.

Turning to FIGS. 13 to 18 showing a third embodiment of the present invention, the same portions as those of the foregoing embodiments are designated at the common reference numerals so that their repeated description is omitted. According to this third embodiment, the working mold 3 is given a sealing structure which is composed of a sealing packing made of heat resisting synthetic rubber or the like. More specifically, this sealing structure is composed of: an annular first sealing member 15A of a circular section sandwiched between the abutting faces of the top cover member 6 and the upper ring member 7; a linear second sealing member 16A of a circular section sandwiched between the abutting faces of the upper ring member 7 and the lower ring member 8; and an annular third sealing member 17A of a rectangular section sandwiched between the abutting faces of the lower ring member 8 and the bottom cover member 9. Of these: the first sealing member 15A is fitted in a groove 32 which is formed in the top cover member 6 and positioned inside of the fixing portions or positioning portions, as shown in FIGS. 14 and 16; the second sealing member 16A is fitted in a groove 33 which is formed in the upper ring member 7 inside of the fixing portions or positioning portions, as shown in FIGS. 14 and 17; and the third sealing member 17 is fitted in a groove 34 which is formed in the bottom cover member 9 inside of the fitting portions or positioning portions, as shown in FIGS. 14 and 18. The third sealing member 17 is further formed with a plurality of rows of annular ridges 35. Thus, in the present embodiment, the cavity 28 in the plaster molds 25 and 22 can be charged under a predetermined vacuum with the resin 30. As a result, the air and gases in the cavity 28 can be sucked and discharged from the discharge port 11 so that the resin 30 having filled up the cavity 28 can be restrained from containing the aforementioned gases or the like. At the same time, the resin 30 can be allowed to smoothly flow into every corners of the cavity 28 to reduce the residual stress in the cooled molding. Moreover, as the resin injection pressure can be lowered as in the foregoing embodiments, the molding machine can be small-sized to suppress the residual stress. Since the molding temperature can be lowered, still moreover, it is possible to produce a molding which can have an excellent molding accuracy and a clear color.

Figure 19:
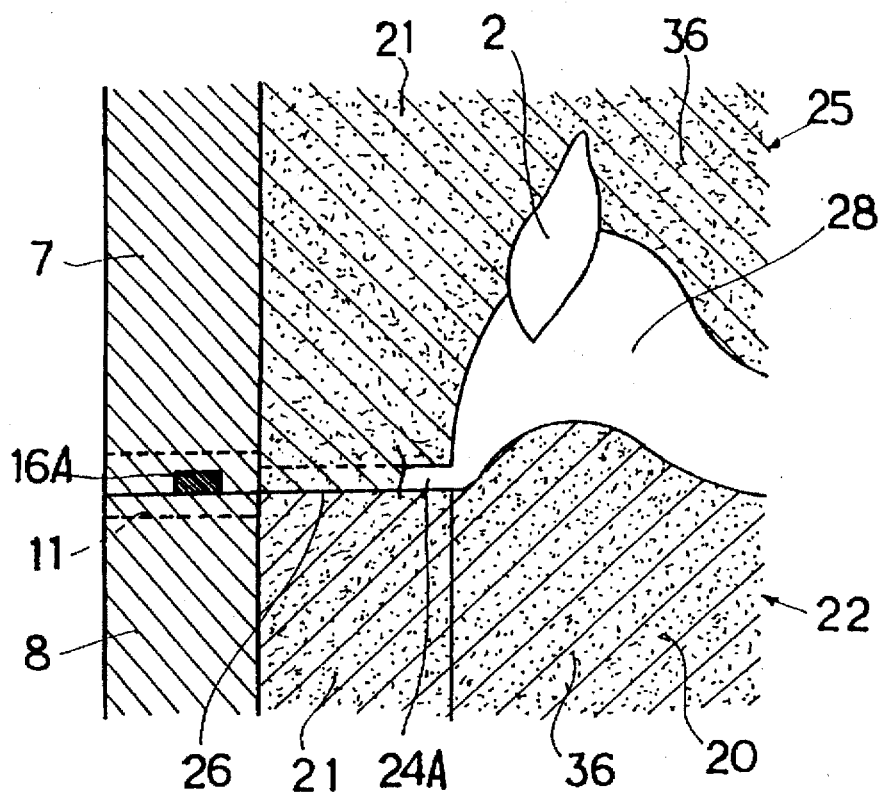
FIG. 19 is an enlarged vertical section showing an essential portion of a fourth embodiment of the present invention.

Turning to FIG. 19 showing a fourth embodiment of the present invention, the same portions as those of the foregoing embodiments are designated at the common reference numerals so that their repeated description is omitted. Specifically, the plaster molds 25 and 22 have their plaster 21 impregnated with a resin 36 or the like, and this resin 36 is solidified. As a result, the plaster molds 25 and 22 thus impregnated with the resin 36 can be improved in gastightness to omit the sealing members more easily. Thus, the working mold can be cleared of all the sealing members, if desired so.

Figure 20:
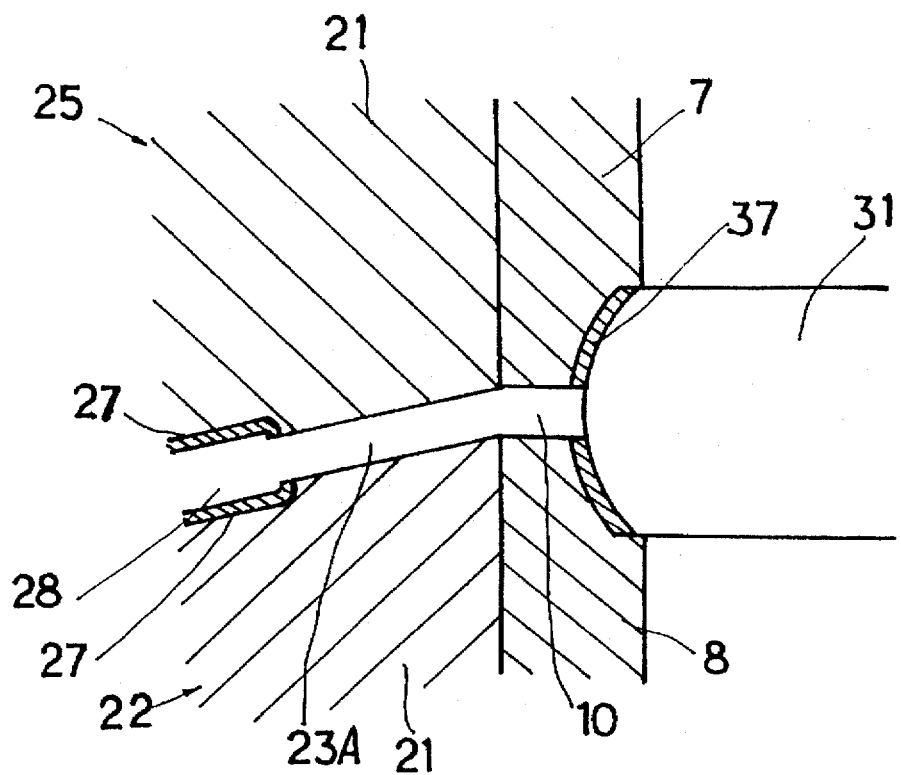
FIG. 20 is an enlarged vertical section showing an essential portion of a fifth embodiment of the present invention.

Turning to FIG. 20 showing a fifth embodiment of the present invention, the same portions as those of the foregoing embodiments are designated at the common reference numerals so that their repeated description is omitted. Specifically, a sealing member 37 is fitted around the injection port 10 of the working mold 3, namely, the portion where the injection port 10 abuts against the leading end of the injection member 31 of the molding machine. The sealing member 37 can retain the gas-tightness at the injection port 10. The entire gas-tightness can be further enhanced by adding the sealing member 37 to any of the sealing structures of the foregoing embodiments. Incidentally, the sealing member 37 can be formed by using the aforementioned surfacing agent or a variety of members having gas-tightness.

Figure 6:
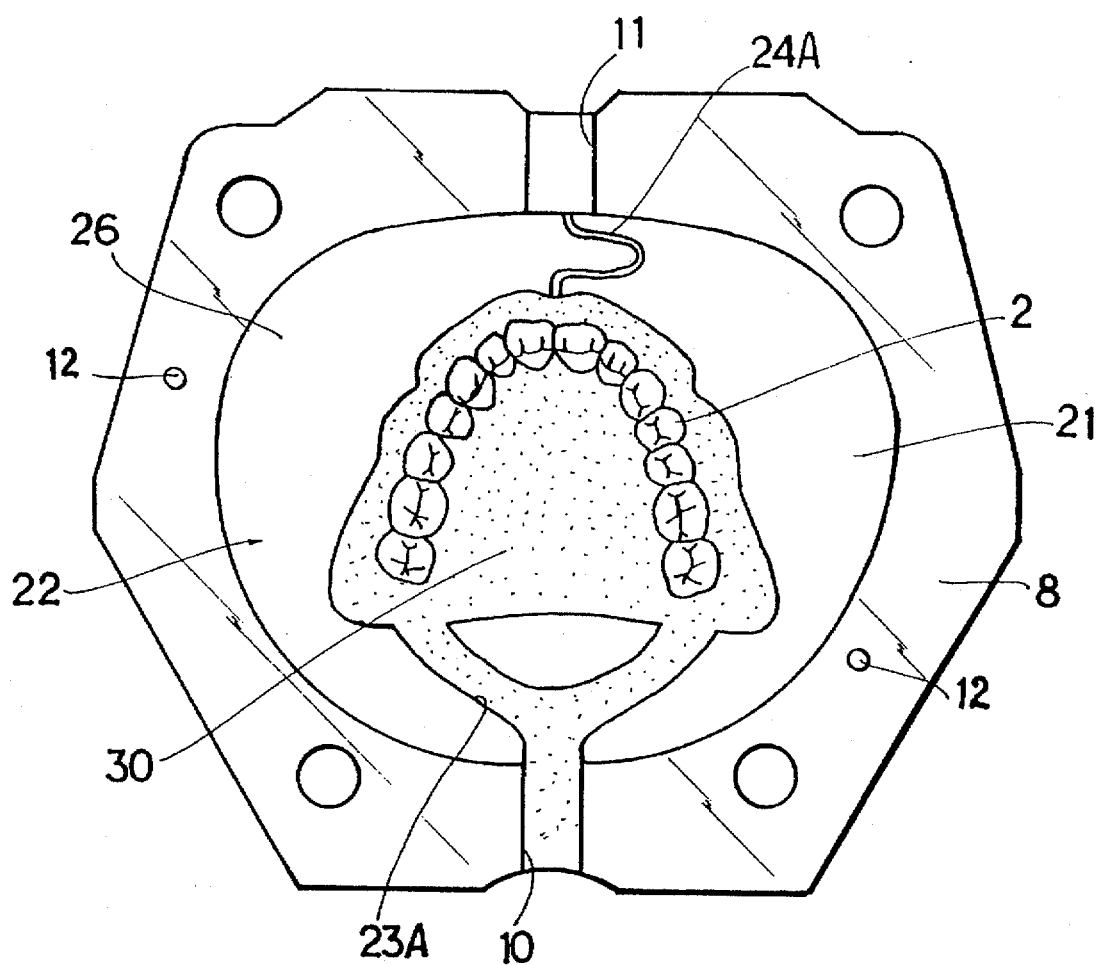
FIG. 6 is a top plan view showing the first embodiment of the present invention.
Figure 7:
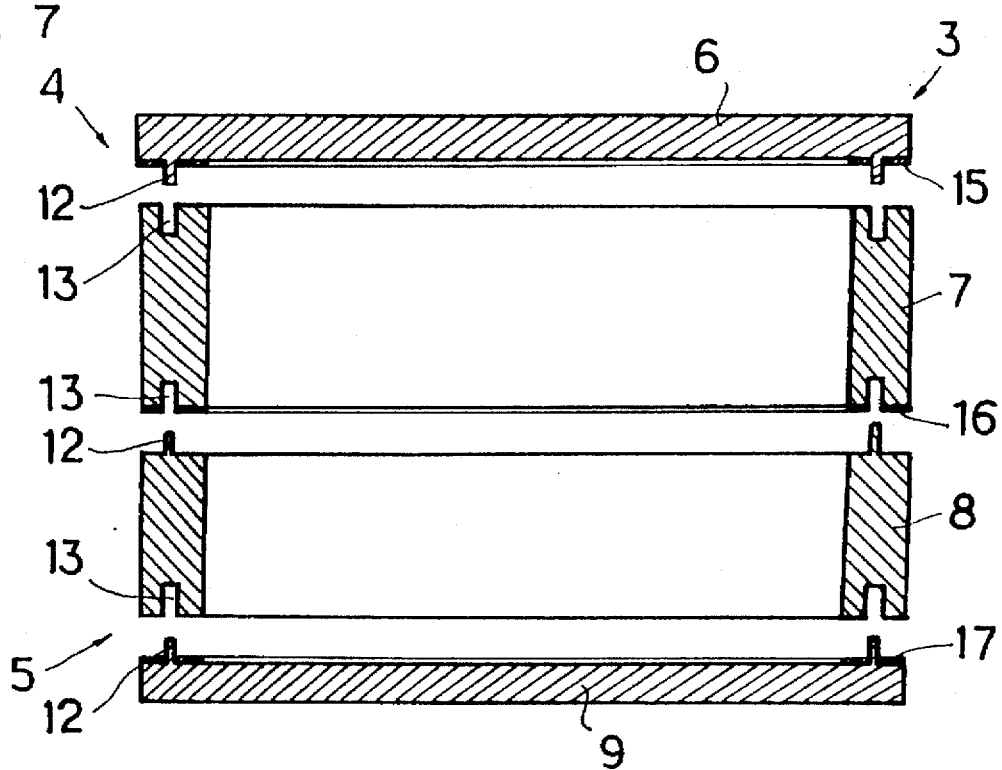
FIG. 7 is an exploded vertical section showing a working mold according to the first embodiment of the present invention.
Figure 8:
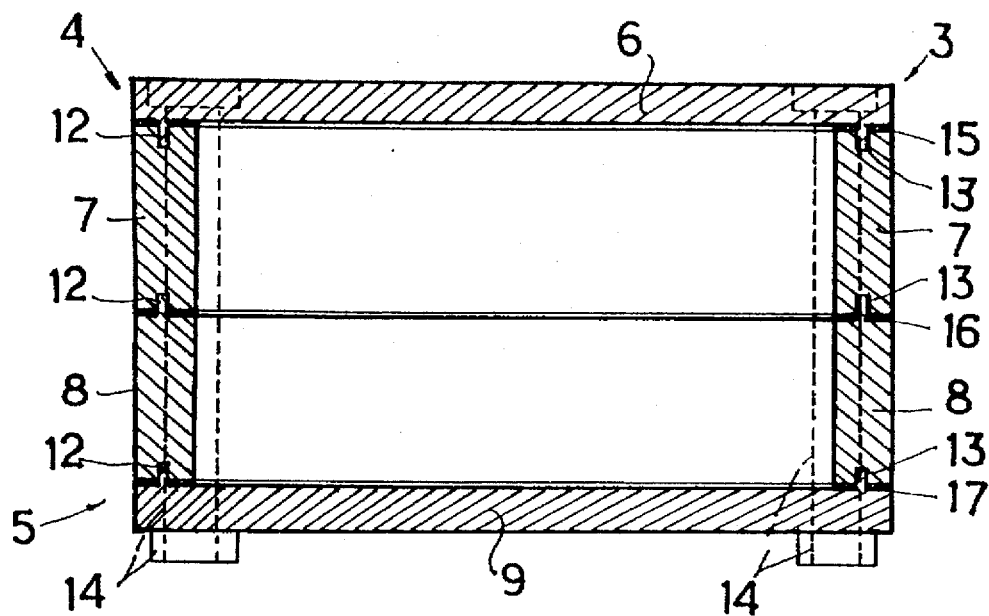
FIG. 8 is a vertical section showing the working mold according to the first embodiment of the present invention.
Figure 9:
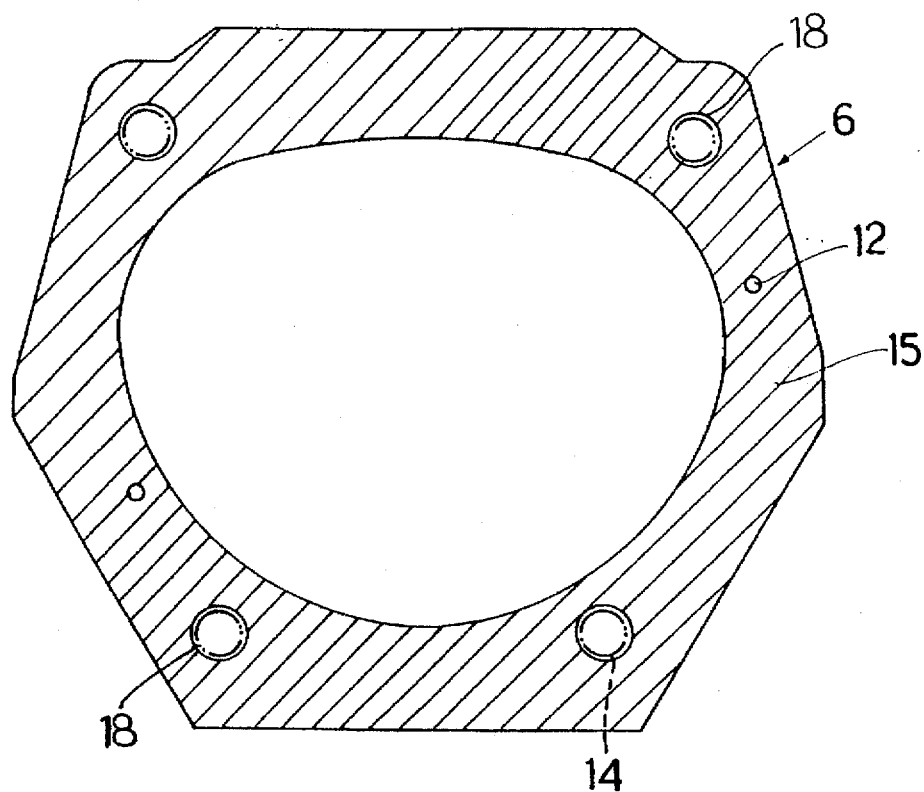
FIG. 9 is a horizontal section showing a top cover member of the working mold according to the first embodiment of the present invention.
Figure 10:
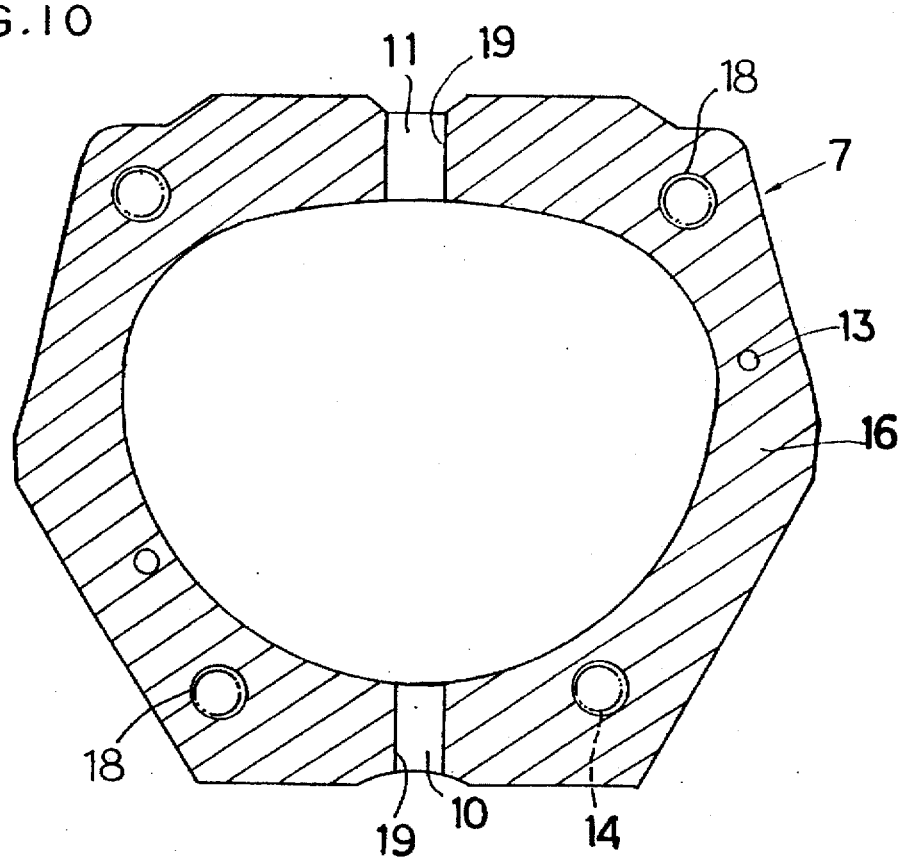
FIG. 10 is a horizontal section showing an upper ring member of the working mold according to the first embodiment of the present invention.
Figure 11:
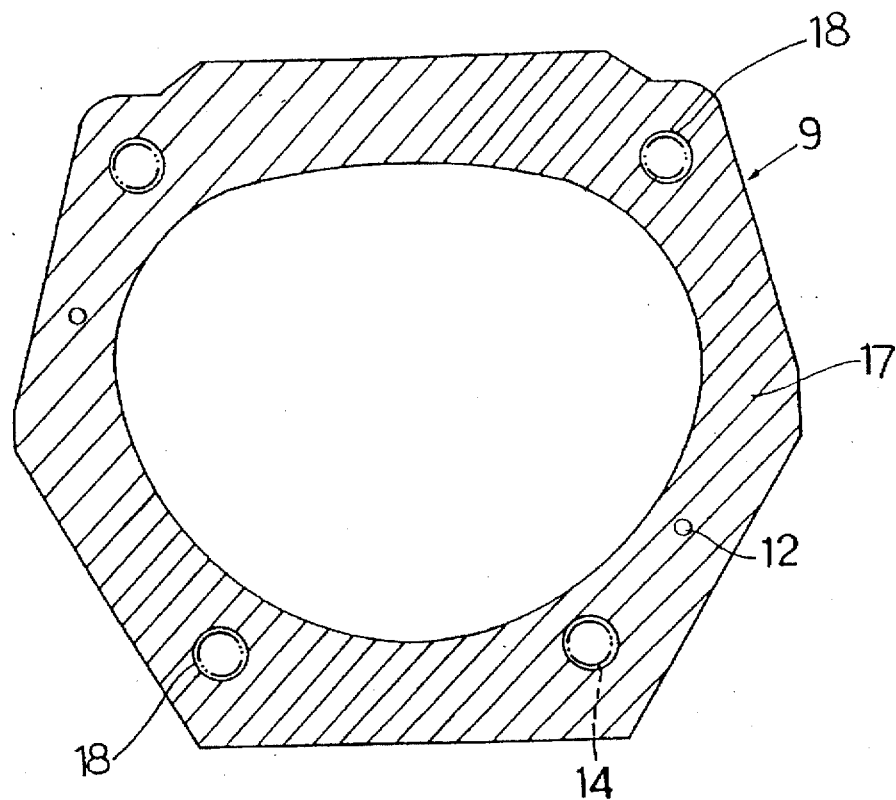
FIG. 11 is a horizontal section showing a bottom cover member of the working mold according to the first embodiment of the present invention.

In a sixth embodiment of the present invention, although not shown, the cavity 28 in the plaster molds 25 and 22 and the discharge port 11 are connected via a plurality of gates, as should be referred to FIG. 6. Moreover, the model 1 and the discharge port 11 are also connected via a plurality of air vents 24. Then, the cavity 28 is charged under a predetermined vacuum with the resin 30. If the air vents 24 are oriented in suitable directions, the charged resin 30 can uniformly flow in the cavity 28 to produce a highly accurate molding.

Figure 21:
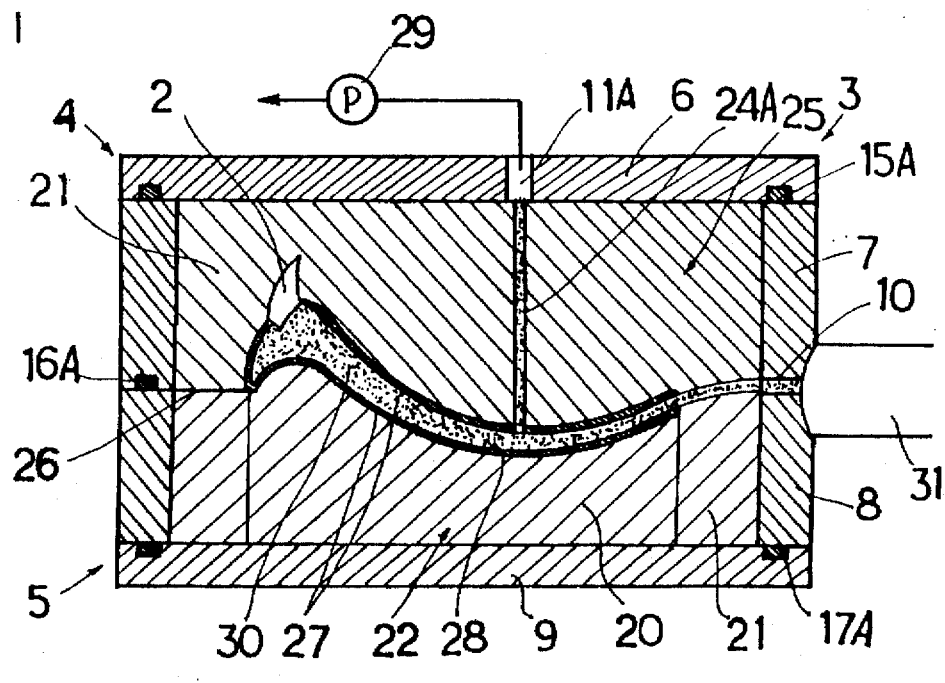
FIG. 21 is a vertical section showing a seventh embodiment of the present invention.

Turning to FIG. 21 showing a seventh embodiment of the present invention, the same portions as those of the foregoing embodiments are designated at the common reference numerals so that their repeated description is omitted. Specifically, the first mold body 4 has its top cover member 6 formed with a discharge port 11A. This discharge port 11A is connected on one hand to the central upper portion of the cavity 28 via the air vent 24A and on the other to the vacuum pump 29. Thus, the discharge port 11A is formed in the top cover member 6 so that the cavity 28 is charged under a predetermined vacuum with the resin 30, to provide effects similar to those of the first embodiment. Alternatively, however, the discharge port may be formed in the bottom cover member 9 of the second mold body 5 and connected to the cavity.

Figure 22:
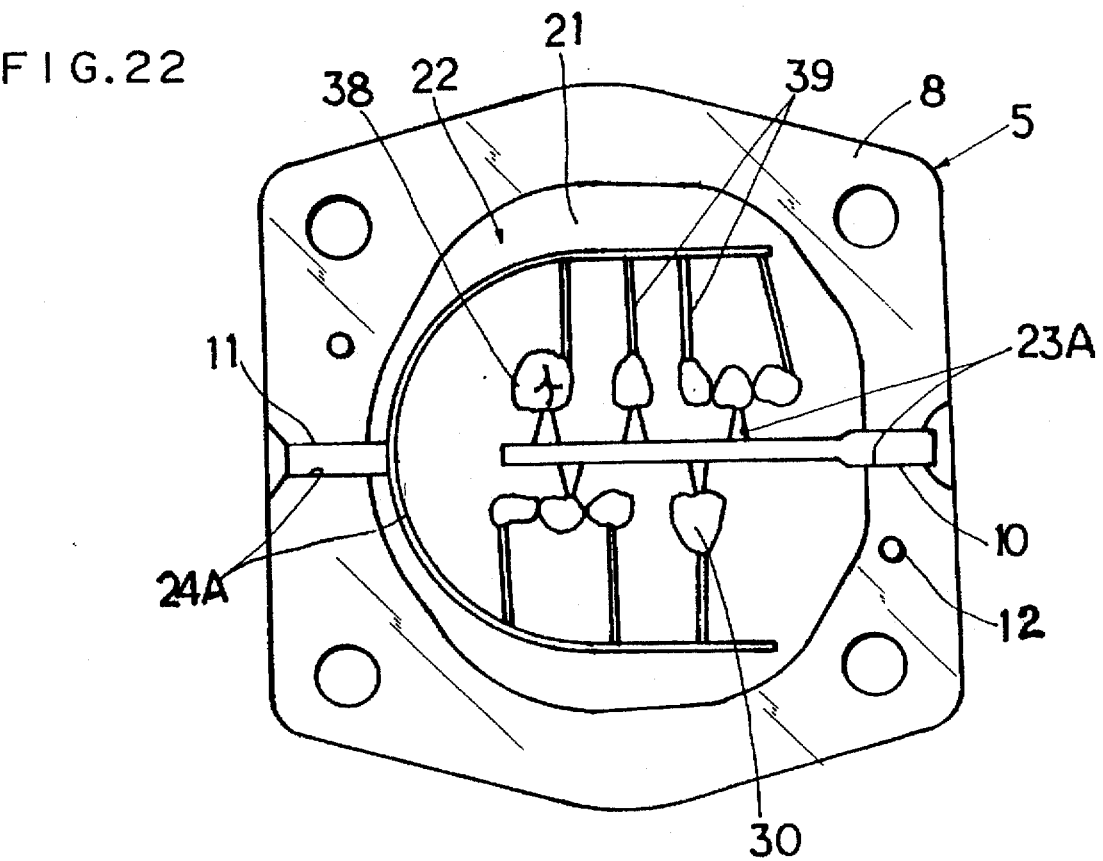
FIG. 22 is a top plan view showing an eighth embodiment of the present invention.

Turning to FIG. 22 showing an eighth embodiment of the present invention, the same portions as those of the foregoing embodiments are designated at the common reference numerals so that their repeated description is omitted. Specifically, the present embodiment is directed to a molding of a medical prosthetic article such as an artificial tooth crown. A plurality of models 38 are formed of a thermoplastic material to have the shapes of artificial crowns and are primarily buried with the plaster wax 21 in the second mold body 5. These models 38 are connected via passages 39 of a thermoplastic material to the injection port 10 by way of sprue runners 23A. The passages 39 are connected on the other hand to the discharge port via the air vent 24A. Next, the upper ring member 7 is assembled and is charged with the plaster wax 21 to bury the models 38 secondarily. As the plaster wax 21 solidifies, the first and second plaster molds 25 and 22 are released and opened to melt, discharge and wash away the models 38, the passages 39, the sprue runners 23A and the air vent 24A so that the cavities shaped to the artificial tooth crowns are left between the plaster molds 25 and 22. These molds 25 and 22 are then closed gas-tight through a suitable one of the seal structures of the foregoing embodiments. The cavities are charged with the resin 30 after they have been or while being evacuated to a predetermined vacuum by the vacuum pump 29. Thus, in the case of the present embodiment, in which the medical prosthetic articles or artificial tooth crowns are to be molded, the plaster molds 25 and 22 are sealed up from the ambient air when they are closed so that the cavities in the plaster molds 25 and 22 can be charged under the predetermined vacuum with the resin 30. As a result, the resin 30 having filled up the cavities can be restrained from containing the gases or the like. At the same time, the resin 30 can be allowed to smoothly flow into every corners of the cavities to reduce the residual stress in the cooled molding so that the residual strain can be suppressed. Moreover, as the resin injection pressure can be lowered as in the foregoing embodiments, the molding machine can be small-sized to suppress the residual stress. Since the molding temperature can be lowered, still moreover, it is possible to produce a molding which can have an excellent molding accuracy and a clear color.

Figure 23:
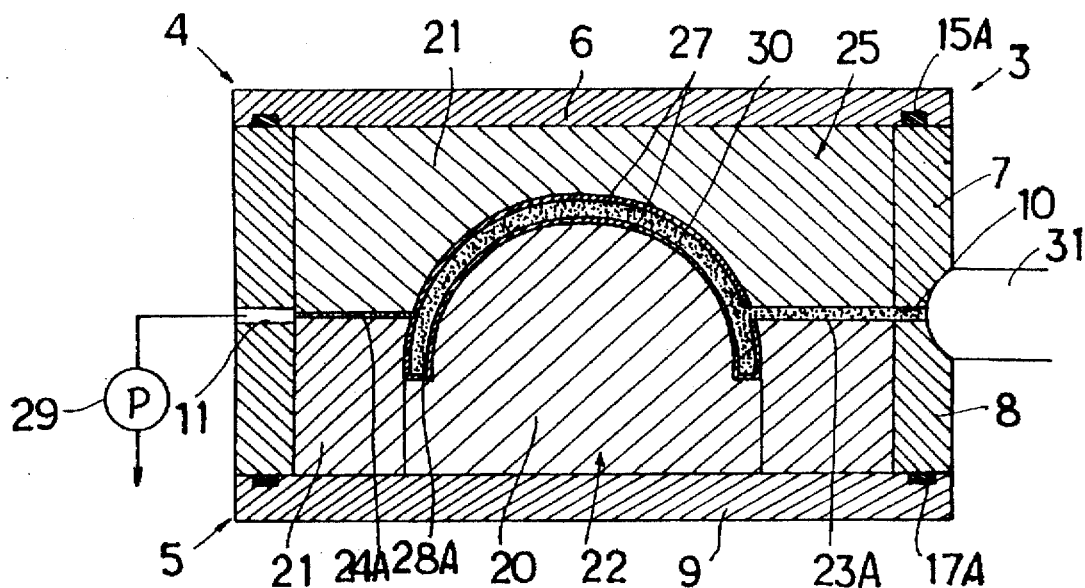
FIG. 23 is a vertical section showing a ninth embodiment of the present invention.

Turning to FIG. 23 showing a ninth embodiment of the present invention, the same portions as those of the foregoing embodiments are designated at the common reference numerals so that their repeated description is omitted. Specifically, the present embodiment if directed to a molding of a medical prosthetic article such as an artificial component to be fitted in an artificial limb. A not-shown model is so formed of a thermoplastic material as to conform to the portion of an artificial leg or hand, in which the artificial component is to be fitted. A cavity 28A is formed to have the shape of the model in the plaster molds 25 and 22. Then, the cavity 28A is charged with the resin 30 to mold the fitting component, after having been or while being evacuated to a predetermined vacuum via the discharge port 11 and the air vent 24A by the vacuum pump 29. Thus, in the case of the present embodiment, in which the medical prosthetic article or artificial limb component is to be molded, the plaster molds 25 and 22 are sealed up from the ambient air when they are closed so that the cavity 28A in the plaster molds 25 and 22 can be charged under the predetermined vacuum with the resin 30. As a result, the resin 30 having filled up the cavity 28A can be restrained from containing the gases or the like. At the same time, the resin 30 can be allowed to smoothly flow into every corners of the cavity 28A to reduce the residual stress in the cooled molding so that the residual strain can be suppressed. Moreover, as the resin injection pressure can be lowered as in the foregoing embodiments, the molding machine can be small-sized to suppress the residual stress. Since the molding temperature can be lowered, still moreover, it is possible to produce a molding which can have an excellent molding accuracy and a clear color.

Figure 24:
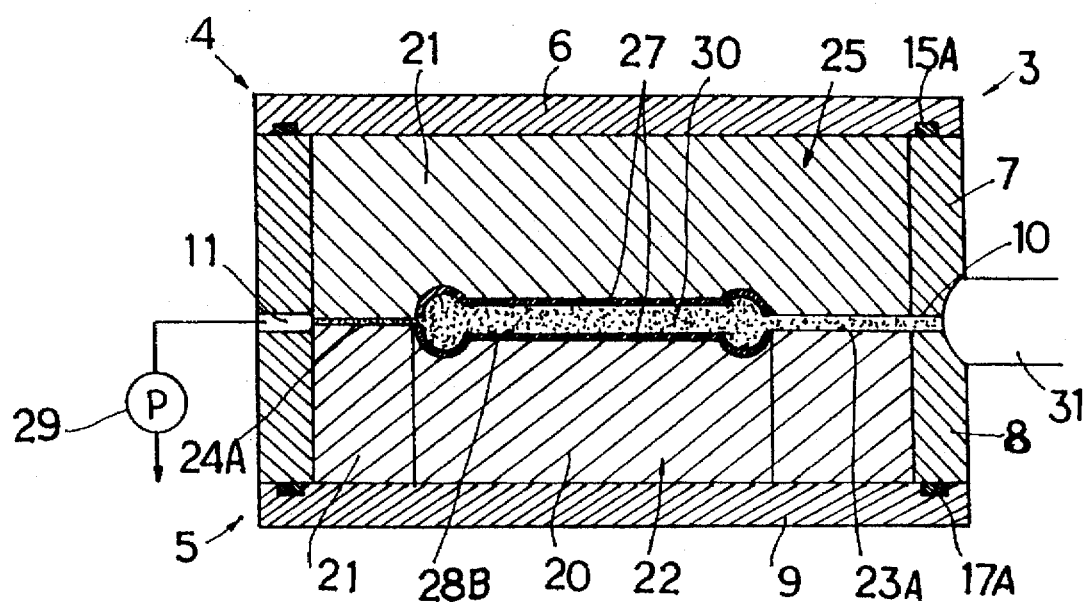
FIG. 24 is a vertical section showing a tenth embodiment of the present invention.

Turning now to FIG. 24 showing a tenth embodiment of the present invention, the same portions as those of the foregoing embodiments are designated at the common reference numerals so that their repeated description is omitted. Specifically, the present embodiment is directed to a molding of a medical prosthetic article such as an artificial long bone, as in the foregoing ninth embodiment. A cavity 28B can be filled up at its every corners with the resin 30, as in the foregoing embodiments.

Figure 25:
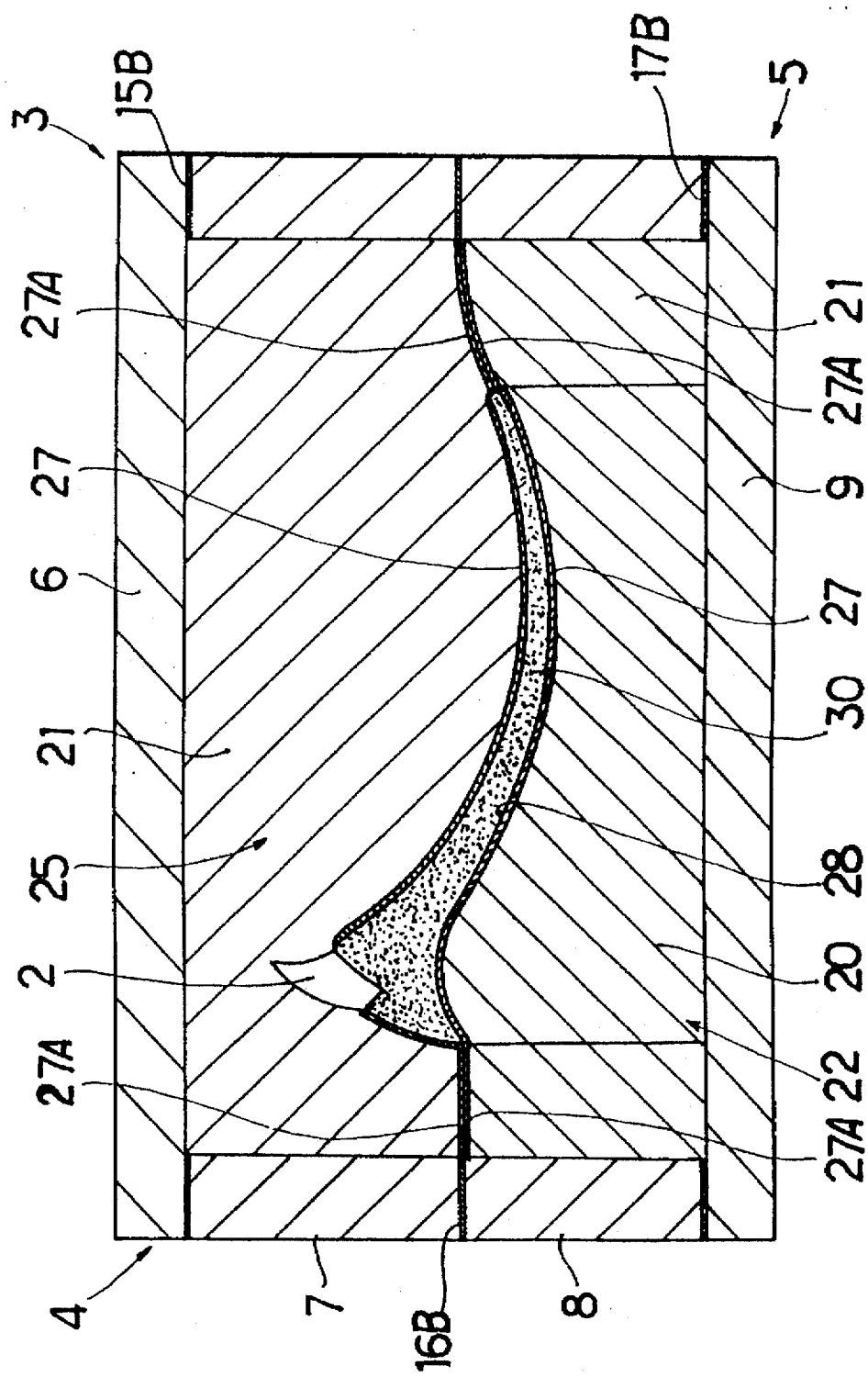
FIG. 25 is a vertical section showing an eleventh embodiment of the present invention.

Turning now to FIG. 25 showing an eleventh embodiment of the present invention, the same portions as those of the foregoing embodiments are designated at the common reference numerals so that their repeated description is omitted. Specifically, the present embodiment is directed to the case, in which the sealing layers 27 and 27A are formed all over the surfaces of the 25 and 22 in the first embodiment. As a result, the working mold 3 can have its sealing structure simplified. Incidentally, in the present embodiment, the sealing structure has its sealing members 15B, 16B and 17B formed of sealing layers by coating a sealing agent of a thermoplastic resin or the like. However, all of these sealing members 15B to 17B may be eliminated.

Figure 26:
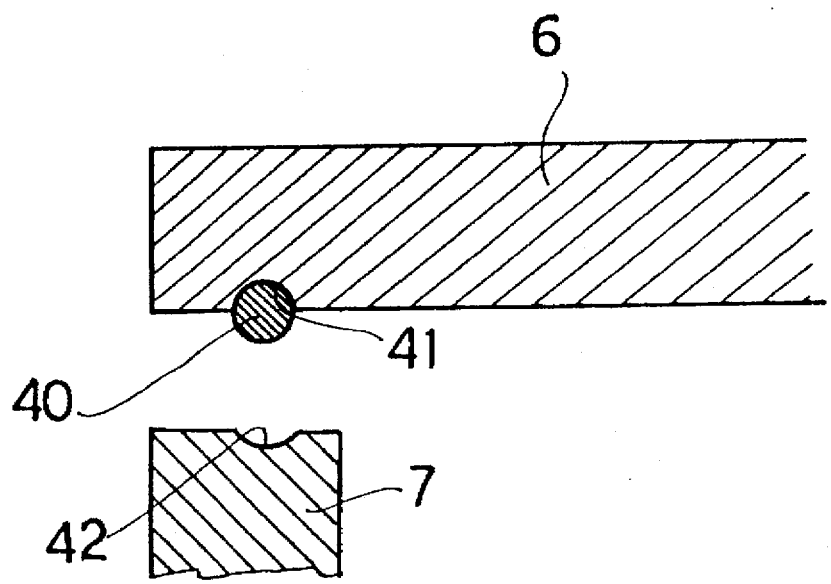
FIG. 26 is a vertical section showing a twelfth embodiment of the present invention.
Figure 27:
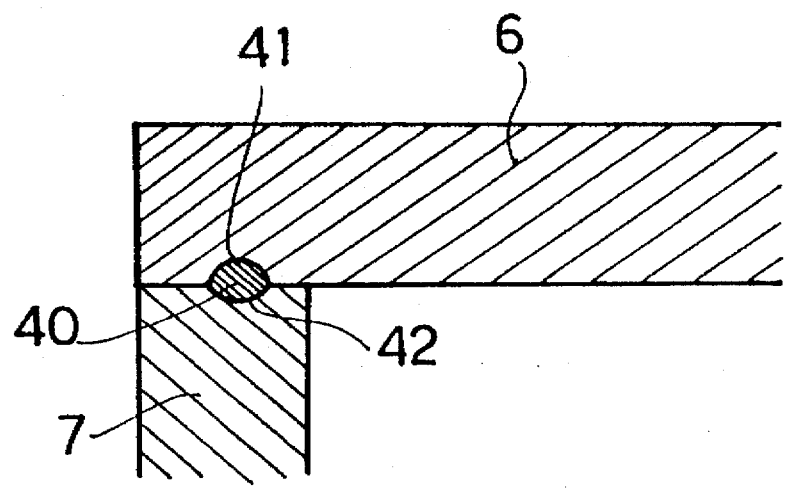
FIG. 27 is a vertical section showing the twelfth embodiment of the present invention.

Turning to FIGS. 26 and 27 showing a twelfth embodiment of the present invention, the same portions as those of the foregoing embodiments are designated at the common reference numerals so that their repeated description is omitted. Specifically, the present embodiment is directed to the case in which a sealing structure for the working mold 3 is to be formed by using a sealing member 40 having a circular section, as in the fourth embodiment. In this case, the sealing member 40 is fitted in a semicircular groove 41 which is formed in the top cover member 6. At the same time, the upper ring member 7 is formed with a groove 42 shallower than the foregoing groove 41, so that the sealing member 40 may be compressed by the shallower groove 42 when the working mold 3 is integrated. Incidentally, this sealing structure may be applied to all the divided portions of the working mold 3.

Figure 28:
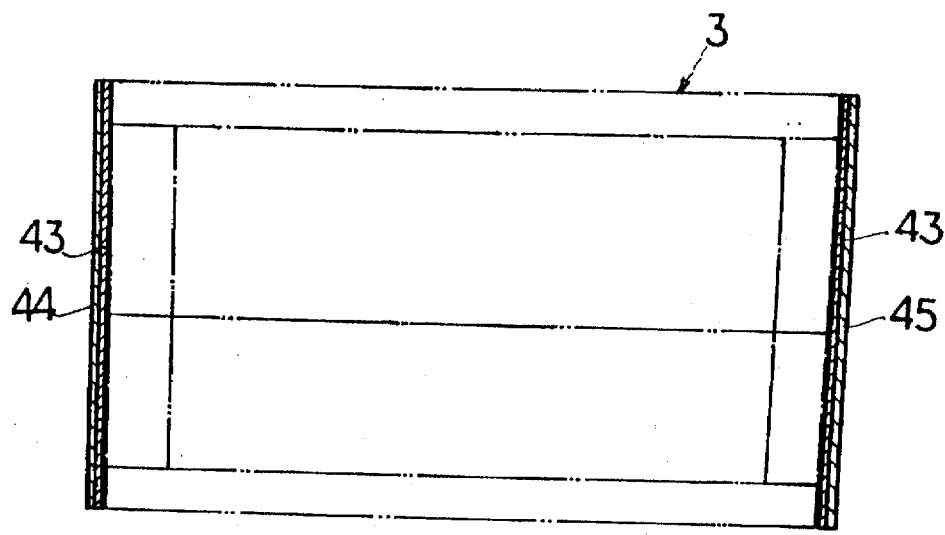
FIG. 28 is a vertical section showing a thirteenth embodiment of the present invention.
Figure 29:
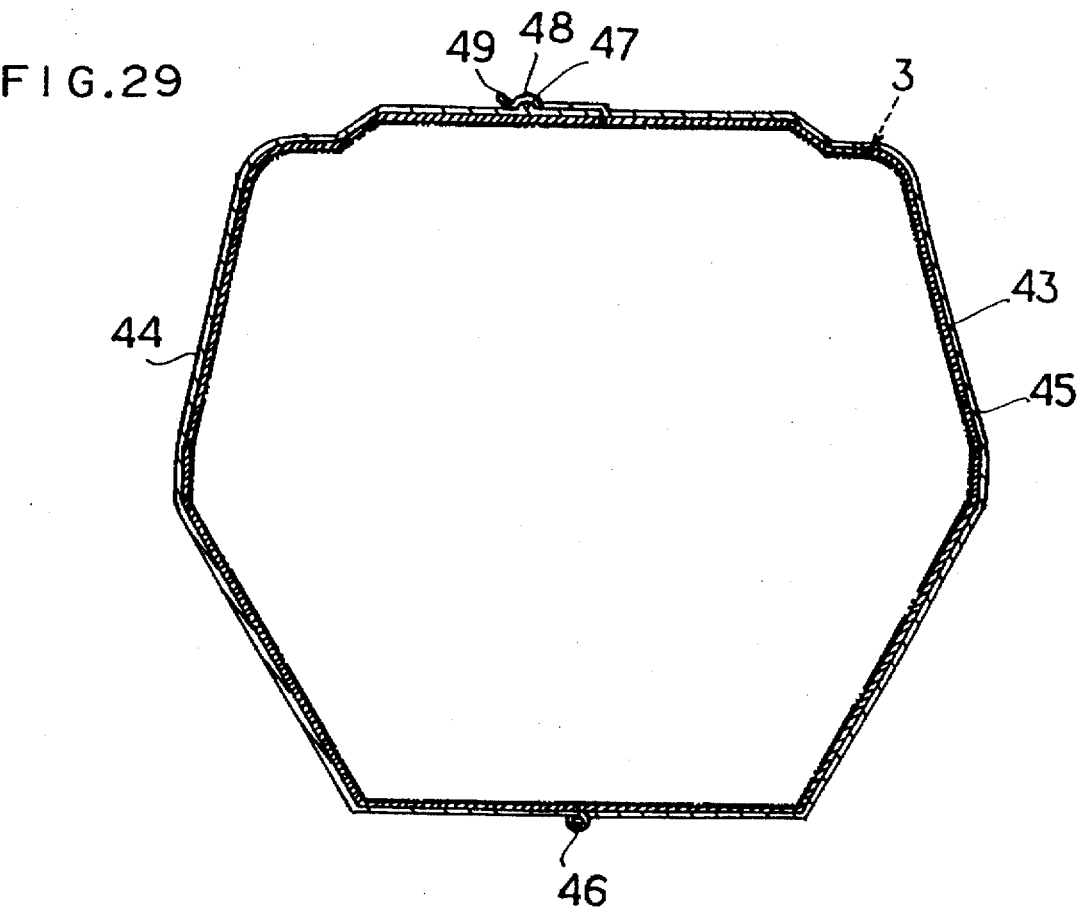
FIG. 29 is a vertical section showing the thirteenth embodiment of the present invention.

Turning to FIGS. 28 and 29 showing a thirteenth embodiment of the present invention, the same portions as those of the foregoing embodiments are designated at the common reference numerals so that their repeated description is omitted. Specifically, the present embodiment is directed to the case, in which the sealing structure is constructed by covering the side peripheries of the divided portions of the working mold 3 with a sealing member 43. This sealing structure is further composed of two divided covers 44 and 45 of a synthetic resin or metal, which are shaped and sized to cover together the side periphery of the working mold 3 substantially in its entirety. These two covers 44 and 45 have their one-end portions hinged at 46, and one cover 44 has its other end formed with a retaining projection 47 whereas the other cover 45 has its other end formed with a retaining recess 48, from which is extended a knob 49. The aforementioned sheet-shaped sealing member 43 is adhered to the inner faces of the two covers 44 and 45. Thus, these covers 44 and 45 are closed on their hinged portions 46 to cover the side periphery of the working mold 3 and are retained by snapping the retaining projection in the retaining recess 48 to seal up the divided portions of the working mold 3.

Figure 30:
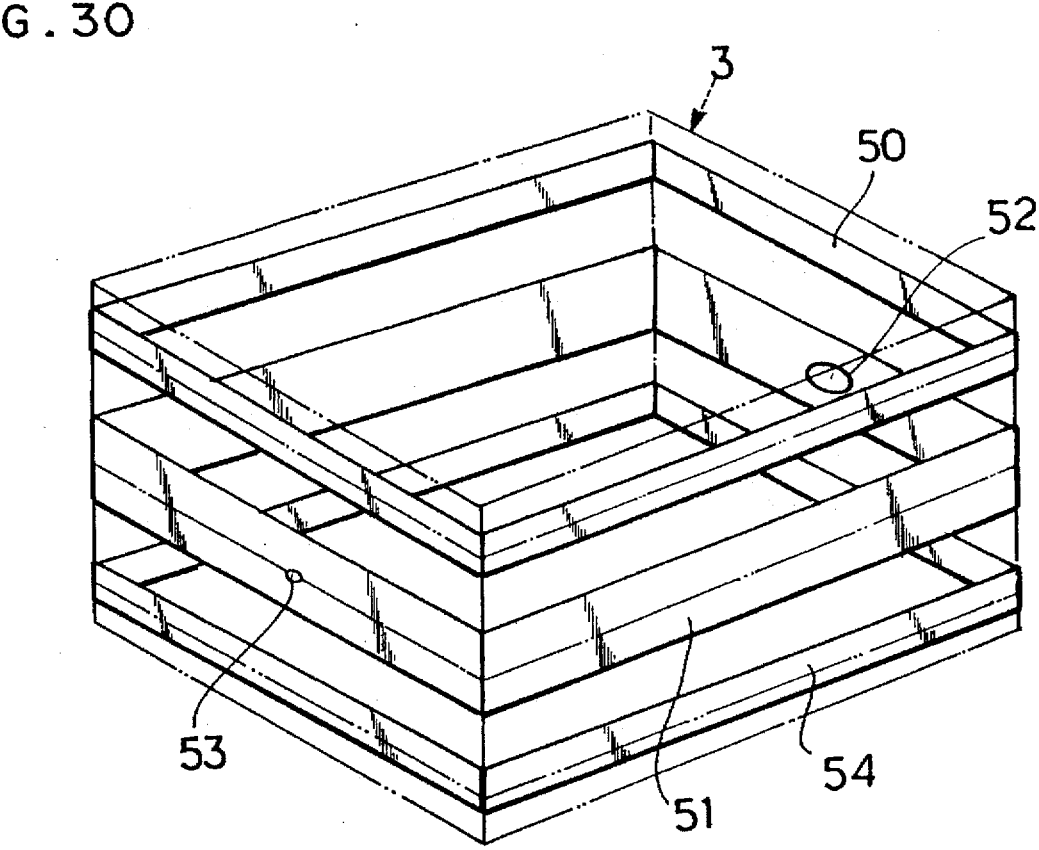
FIG. 30 is a perspective view showing a fourteenth embodiment of the present invention.

Turning to FIG. 30 showing a fourteenth embodiment of the present invention, the same portions as those of the foregoing embodiments are designated at the common reference numerals so that their repeated description is omitted. Specifically, the present embodiment is directed to the case, in which elastic sealing members 50, 51 and 54 framed to fit the side periphery of the working mold 3 are removably fixed on the side peripheries of the individual divided portions of the working mold 3. In this embodiment, the working mold 3 is formed into a rectangular shape, as shown, and the sealing member 51 is formed with a hole 52 for the injection member 31 and a hole 53 for the discharge port 11. Thus, the sealing effect can be achieved by fitting the sealing members 54, 51 and 50 elastically in the recited order on the side peripheries of the individual divided portions of the working mold 3 integrated.

Figure 31:
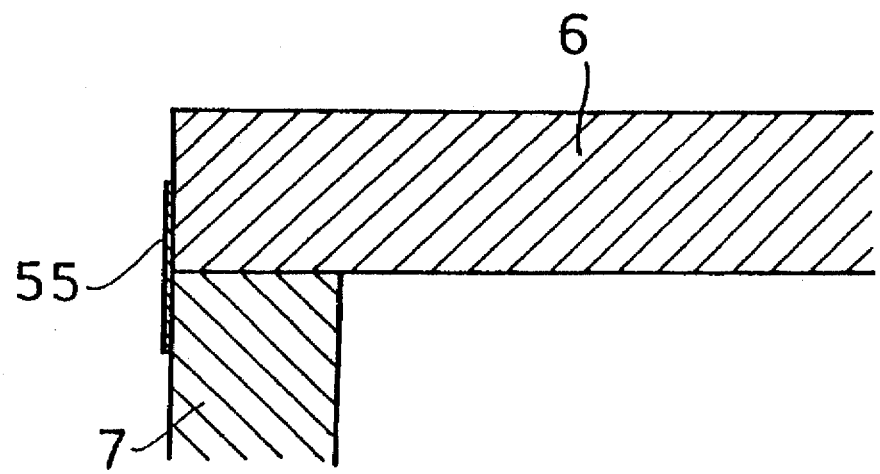
FIG. 31 is an enlarged vertical section showing an essential portion of a fifteenth embodiment of the present invention.

Turning to FIG. 31 showing a fifteenth embodiment of the present invention, the same portions as those of the foregoing embodiments are designated at the common reference numerals so that their repeated description is omitted. Specifically, the present embodiment is constructed such that the sealing structure is made by adhering a sealing member or sealing tape 55 peelably to the side periphery of each of the divided portions of the working mold 3.

Figure 32:
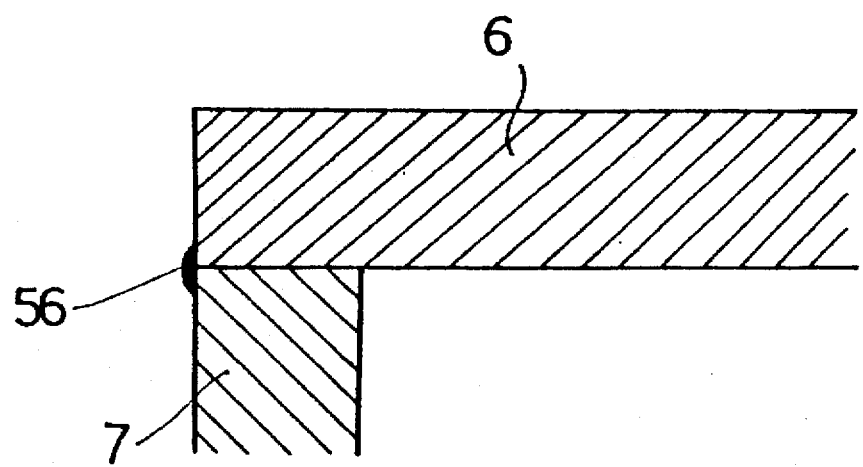
FIG. 32 is an enlarged vertical section showing an essential portion of a sixteenth embodiment of the present invention.

Turning to FIG. 32 showing a sixteenth embodiment of the present invention, the same portions as those of the foregoing embodiments are designated at the common reference numerals so that their repeated description is omitted. Specifically, the present embodiment is constructed such that the sealing structure is made by removably applying a sealing member 56 to the side periphery of each of the divided portions of the working mold 3.

The present invention should not be limited to the foregoing embodiments but can be modified in various manners within the gist thereof. For example, the present invention can be applied to various moldings of medical prosthetic articles such as artificial bones, and the denture bases may be either whole or partial. Still moreover, the high-molecular resin to be employed can be exemplified by a polycarbonate resin, a polyolefin resin or a polysulfone resin. In the embodiments having no sealing layer on the plaster mold surfaces, furthermore, the model, the sprue runner and the air vent may be melted and discharged by using the method, as disclosed in Japanese Patent Publication No. 2023/1982 or the like, but without dividing the plaster mold. On the other hand, the arranging positions of the sealing members and the position of evacuation can be suitably modified within the gist of the present invention. For example, a suitable selection can be made from the sealing members having a sheet shape, the sealing members made of a packing and the sealing members formed of a sealing layer, and these sealing members can be combined to construct the sealing structure. Although the first and second mold bodies are constructed of the dividable cover members and the ring members, at least one of the mold bodies may have its cover member and ring member united. On the other hand, the sheet-shaped sealing members need not be adhered to the mold bodies but may be removably sandwiched inbetween. Moreover, the sheet-shaped sealing members may have their sizes such as widths suitable selected. Still moreover, the working mold should not have its sealing structure limited to those of the foregoing embodiments but may have the same constructed by suitable means. In the foregoing embodiments, on the other hand, the working mold is closed by the fixing members but may be fixed through a packing. Moreover, the working mold may be closed by a closing device of the molding machine with or without the fixing members.

In a method of manufacturing a medical prosthetic article by charging the cavity of a plaster mold with a resin, according to the present invention, the plaster mold has its cavity sealed up, when closed, from the ambient air and charged under a predetermined degree of vacuum with a resin. Thus, it is possible to provide the medical prosthetic article manufacturing method which can produce a molding having a suppressed molding strain.

What is claimed is:

1. A method of manufacturing a medical prosthetic article by injecting a thermoplastic resin into the cavity of a plaster mold, comprising the steps of:

confining first and second plaster molds having porous structures respectively in first and second mold bodies made dividable from each other, said first and second plaster molds defining therein a cavity having first and second inner faces, a contour of a medical prosthetic article to be molded, a sprue runner communicating with said cavity, and an air vent communicating with said cavity; sealing up said cavity not only from the ambient air but also from said porous structures of said first and second plaster molds, when said first and second mold bodies are closed;

evacuating said cavity through said air vent; and injecting a thermoplastic resin through said sprue runner into said cavity under a predetermined degree of vacuum.

2. A medical prosthetic article manufacturing method according to claim 1, wherein said sealing-up step includes the sub-step of fitting a sealing member between said divided portions of said first and second mold bodies.

3. A medical prosthetic article manufacturing method according to claim 2, wherein said sealing-up step further includes the sub-step of forming a sealing layer on said first and second inner faces of said first and second plaster molds.

4. A medical prosthetic article manufacturing method according to claim 2, wherein said sealing-up step further includes the sub-step of impregnating said first and second plaster molds with a sealing agent.

5. A medical prosthetic article manufacturing method according to claim 1, wherein said sealing-up step includes the sub-step of covering the peripheries of said first and second mold bodies with a sealing member.

6. A medical prosthetic article manufacturing method according to claim 5, wherein said sealing-up step further includes the sub-step of forming a sealing layer on said first and second inner faces of said first and second plaster molds.

7. A medical prosthetic article manufacturing method according to claim 5, wherein said sealing-up step further includes the sub-step of impregnating said first and second plaster molds with a sealing agent.

* * * * *